US012673213B2

(12) United States Patent
Wasserman et al.

(10) Patent No.: US 12,673,213 B2
(45) Date of Patent: \*Jul. 7, 2026

(54) TUMOR TREATING FIELD TRANSDUCERS WITH PROTECTIVE BORDER, AND APPARATUSES AND METHODS FOR ACTIVE DETECTION OF IMPROPER TRANSDUCER CONFIGURATION

(71) Applicant: Novocure GmbH, Root (CH)

(72) Inventors: Yoram Wasserman, Haifa (IL); Stas Obuchovsky, Haifa (IL); Nataliya Kuplennik, Haifa (IL); David Shapiro, Haifa (IL)

(73) Assignee: Novocure GmbH, Baar (CH)

( * ) Notice: Subject to any disclaimer, the term of this patent is extended or adjusted under 35 U.S.C. 154(b) by 297 days.

This patent is subject to a terminal disclaimer.

(21) Appl. No.: 18/216,151

(22) Filed: Jun. 29, 2023

(65) Prior Publication Data

US 2024/0001133 A1    Jan. 4, 2024

Related U.S. Application Data

(60) Provisional application No. 63/421,005, filed on Oct. 31, 2022, provisional application No. 63/420,950, (Continued)

(51) Int. Cl.
*A61N 1/40* (2006.01)

(52) U.S. Cl.
CPC ....................................... *A61N 1/40* (2013.01)

(58) Field of Classification Search
CPC ..... A61N 1/36002; A61N 1/0456; A61N 1/40
See application file for complete search history.

(56) References Cited

U.S. PATENT DOCUMENTS 3,911,906 A    10/1975  Reinhold, Jr.
4,166,465 A    9/1979   Esty et al.
(Continued)

FOREIGN PATENT DOCUMENTS

WO    2017/072706 A1    5/2017
WO    2019/119045 A1    6/2019

OTHER PUBLICATIONS

Eilon D. Kirson et al., "Disruption of Cancer Cell Replication by Alternating Electric Fields," Cancer Res. 2004 64:3288-3295.

*Primary Examiner* — Tammie K Marlen
(74) *Attorney, Agent, or Firm* — McCarter & English, LLP; Michael A. Sartori

(57) ABSTRACT

A transducer apparatus for delivering tumor treating fields to a subject's body, including: a substrate; an electrode element coupled to the substrate; a layer of anisotropic material electrically coupled to the electrode element, wherein the electrode element is located between the substrate and the layer of anisotropic material having a front face and a back face, wherein the back face of the layer of anisotropic material faces the electrode element; a non-conductive material border disposed over an outer perimeter of the layer of anisotropic material, the non-conductive material border being electrically non-conductive, wherein, when viewed in a direction perpendicular to the front face of the layer of anisotropic material: an inner edge of the non-conductive material border overlaps a portion of the front face of the layer of anisotropic material, and an outer edge of the non-conductive material border extends outside the outer perimeter of the layer of anisotropic material.

20 Claims, 14 Drawing Sheets

Related U.S. Application Data filed on Oct. 31, 2022, provisional application No. 63/357,390, filed on Jun. 30, 2022, provisional application No. 63/357,278, filed on Jun. 30, 2022.

(56)                    References Cited

U.S. PATENT DOCUMENTS

| 4,736,752 | A | 4/1988 | Munck et al. |
|---|---|---|---|
| 7,016,725 | B2 | 3/2006 | Palti |
| 7,089,054 | B2 | 8/2006 | Palti |
| 7,333,852 | B2 | 2/2008 | Palti |
| 7,565,205 | B2 | 7/2009 | Palti |
| 7,805,201 | B2 | 9/2010 | Palti |
| 8,244,345 | B2 | 8/2012 | Palti |
| 2007/0239250 | A1 | 10/2007 | Babaev |
| 2020/0038648 | A1 | 2/2020 | Heintz et al. |
| 2020/0101278 | A1 | 4/2020 | Freeman et al. |
| 2021/0146131 | A1 | 5/2021 | Schmidt |
| 2021/0220640 | A1 | 7/2021 | Deslauriers |
| 2021/0346693 | A1 | 11/2021 | Deslauriers |
| 2021/0402179 | A1 | 12/2021 | Wasserman et al. |
| 2023/0037806 | A1 | 2/2023 | Wasserman et al. |
| 2023/0043071 | A1 | 2/2023 | Wasserman et al. |
| 2023/0065587 | A1 | 3/2023 | Shnaiderman et al. |
| 2023/0302289 | A1 | 9/2023 | Halavee et al. |
| 2023/0414931 | A1 | 12/2023 | Shapiro et al. |
| 2024/0001134 | A1 | 1/2024 | Wasserman et al. |
| 2024/0100321 | A1 | 3/2024 | Wasserman et al. |

FIG. 3C
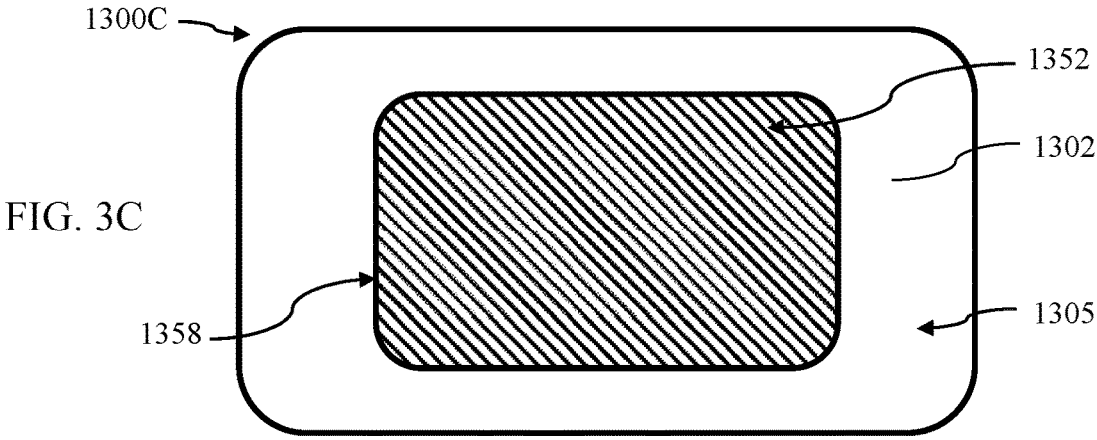
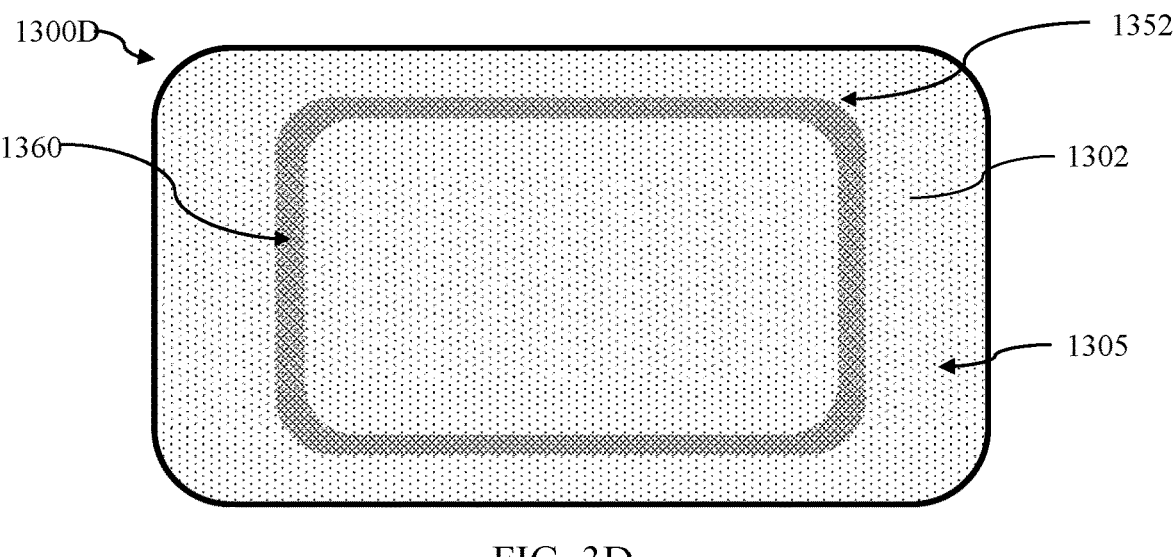
FIG. 3D

TUMOR TREATING FIELD TRANSDUCERS WITH PROTECTIVE BORDER, AND APPARATUSES AND METHODS FOR ACTIVE DETECTION OF IMPROPER TRANSDUCER CONFIGURATION

CROSS-REFERENCE TO RELATED APPLICATIONS

This application claims the benefit of and priority to U.S. Provisional Patent Application No. 63/357,278, filed Jun. 30, 2022; U.S. Provisional Patent Application No. 63/357,390, filed Jun. 30, 2022; U.S. Provisional Patent Application No. 63/420,950, filed Oct. 31, 2022; and U.S. Provisional Patent Application No. 63/421,005, filed Oct. 31, 2022, the contents of each of which are all incorporated herein by reference in their entireties.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. TTFields are induced non-invasively into the region of interest by transducers placed on the patient's body and applying AC voltages between the transducers. Conventionally, transducers used to generate TTFields include a plurality of electrode elements comprising ceramic disks. One side of each ceramic disk is positioned against the patient's skin, and the other side of each disc has a conductive backing. Electrical signals are applied to this conductive backing, and these signals are capacitively coupled into the patient's body through the ceramic discs. Conventional transducer designs include arrays of ceramic disks attached to the subject's body via adhesive or a conductive skin-contact layer such as a hydrogel.

BRIEF DESCRIPTION OF THE DRAWINGS

FIGS. 3A-3D depict example transducers with a visual indicator.

DESCRIPTION OF EMBODIMENTS

Figures 1A, 1B:
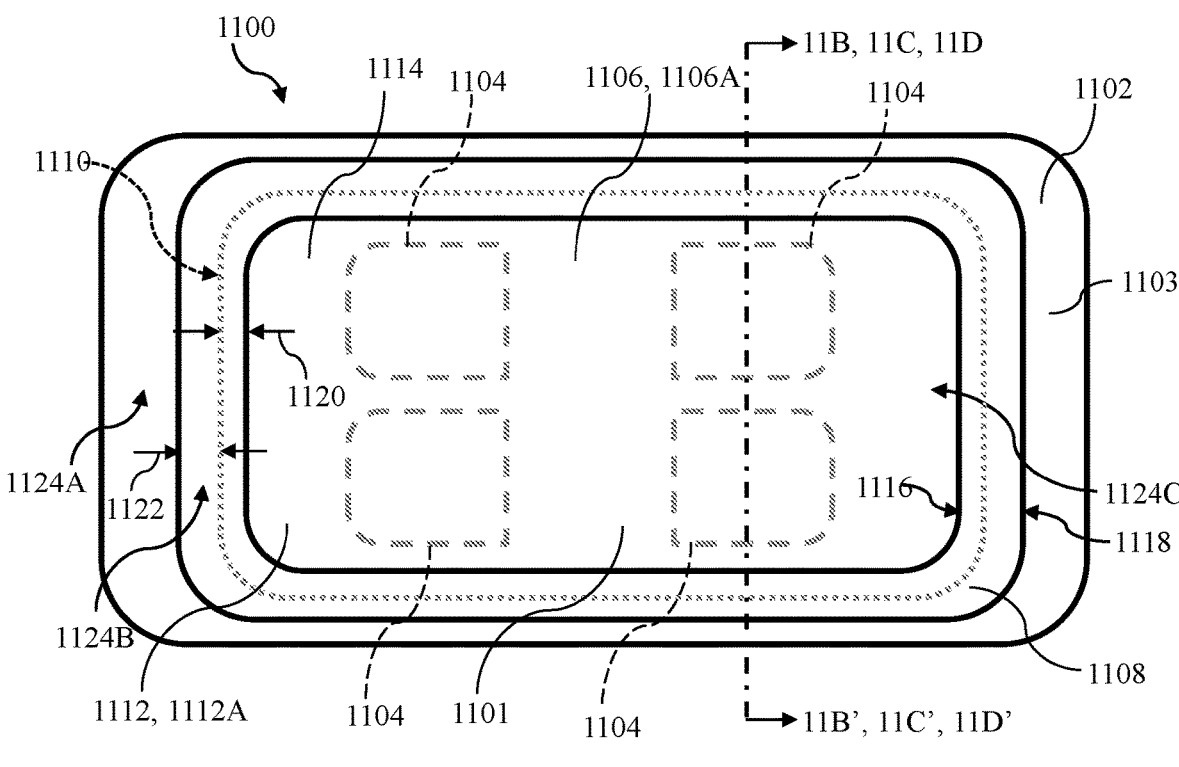
FIGS. 1A-1D depict example transducers with a non-conductive border.

This application describes exemplary transducer apparatuses used to apply TTFields to a subject's body for treating one or more cancers. This application also describes exemplary methods to detect an improper configuration of transducers on a subject's body.

Transducers used to apply TTFields to a subject's body often include multiple electrode elements coupled together on a substrate and attached to the subject's body at a desired location, for example, via an adhesive layer on the substrate or a separately applied adhesive. Transducers can include one or more conductive material layers located between the electrode elements and the subject's body upon attachment of the transducer to the subject's body. Such conductive material layers may include, for example, a conductive skin-contact layer such as a hydrogel or a conductive adhesive layer located against the subject's body. The conductive adhesive layer may take the form of an adhesive matrix material having conductive particles (e.g., carbon fibers or carbon black powder) embedded at least partially in the adhesive matrix material. Additionally, the conductive material layer(s) may include a conductive layer of anisotropic material taking the form of a carbon layer, a graphite layer, or others. The conductive layer of anisotropic material may have different thermal and/or electrical conductivities in a direction perpendicular to a face of the transducer (z-direction) than in directions parallel to the transducer face (directions in the x-y plane). Conductive material layer(s) having greater thermal conductivity in the x-y plane than in the z-direction can spread out heat generated by the electrode elements within an x-y plane while conducting electricity from the electrode elements in a z-direction toward the subject's body. This allows greater currents to be applied to the electrode elements while maintaining the temperature at the subject's skin under a maximum operating temperature.

In general, one or more pairs of transducers are positioned on the subject's body and used to alternately apply TTFields to the subject's body. Generally, it is preferred that there are at least two pairs of transducers, and that the transducers are not touching. However, on certain areas (e.g., the head) of the subject's body, two or more transducers may be positioned such that they overlap one another or are located immediately adjacent one another. It is important to avoid electrical contact between overlapping/adjacent transducers, particularly those with conductive material layer(s) that are highly conductive in the x-y plane, so as to prevent a short circuit in which current runs through the transducers and not through the subject's body. Electrical contact between transducers is typically avoided via physical separation of the conductive elements of the transducers. For example, physical separation is provided by a non-conductive adhesive bandage provided on each transducer, the adhesive bandage extending in the x-y plane beyond the outer edges of the electrode elements and any conductive material layers.

However, subjects will sometimes cut the adhesive bandage of a transducer, either to resize the transducer for fitting on a portion of the subject's body or to reduce the total contact area of the adhesive bandage (which can cause skin irritation) with the subject's body. Cutting the bandage in this manner could lead to the unintentional and undesirable exposure of a conductive material layer. Exposure of a conductive material layer of the transducer may eliminate the physical separation of conductive elements between adjacent transducers, potentially causing a short circuit between the transducers. In addition, cutting the anisotropic layer may reduce the effectiveness of the anisotropic layer in reducing the temperature across the subject's body.

The inventors have now recognized that a need exists for transducers capable of preventing or deterring physical exposure of conductive material layer(s) of the transducer to a conductive portion of a nearby transducer. In particular, a need exists for transducers that are capable of preventing or deterring a user from cutting the transducer in a way that physically exposes conductive material layer(s) of the transducer. The inventors have additionally recognized that a need exists for transducer apparatuses and methods for actively detecting an improper configuration of one or more transducers on the subject's body and alerting a user to the improper configuration. The improper configuration could represent a single transducer being cut such that one or more conductive material layers are exposed in the x-y plane. The improper configuration may result from the physical exposure of conductive material layer(s) of the transducer to a conductive portion of a nearby transducer. Alerting a user to the improper configuration of one or more transducers may help to prevent a short circuit between transducers on the subject's body.

Exemplary transducer apparatuses include at least one of: a non-conductive border, a visual indicator, or a cut-resistant material layer. The non-conductive border may prevent exposure of the edges of a conductive portion (e.g., a conductive layer of anisotropic material and/or a conductive portion of the adhesive layer) of the transducer and, as such, may prevent two transducers from electrically connecting. The visual indicator may deter a user from cutting the transducer in a way that exposes the conductive portion of the transducer. The cut-resistant material layer may prevent a user from cutting parts of the transducers that would expose the conductive portion of the transducer.

Some embodiments involve active detection of a physical cut in a transducer or a short between transducers, and such a detection may be useful to know prior to providing signals to the transducers to generate TTFields. As an example, to actively detect a physical cut in a transducer, the transducer may include a wire around a footprint of the transducer's active area, and a detected short in the wire may indicate that both the wire and the transducer's active area have been cut by the user. As an example, to actively detect a short between two transducers, electrical measurements (e.g., voltage, or voltage and current) between two transducers may be obtained, and calculated parameters may be compared to a threshold to determine if a short exists between the two transducers.

Figure 1C:
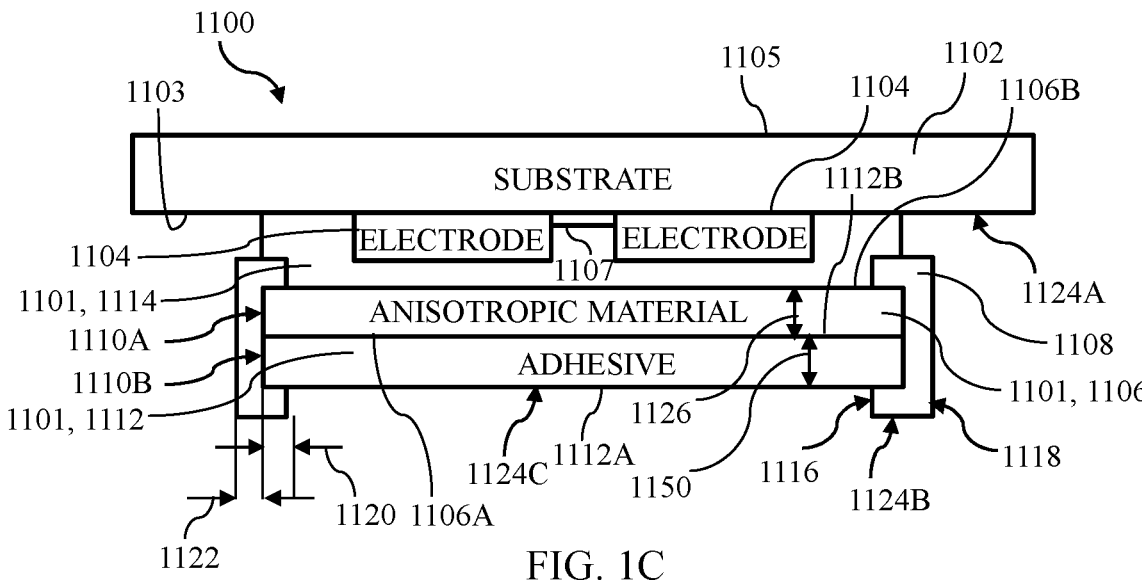
Figure 1D:
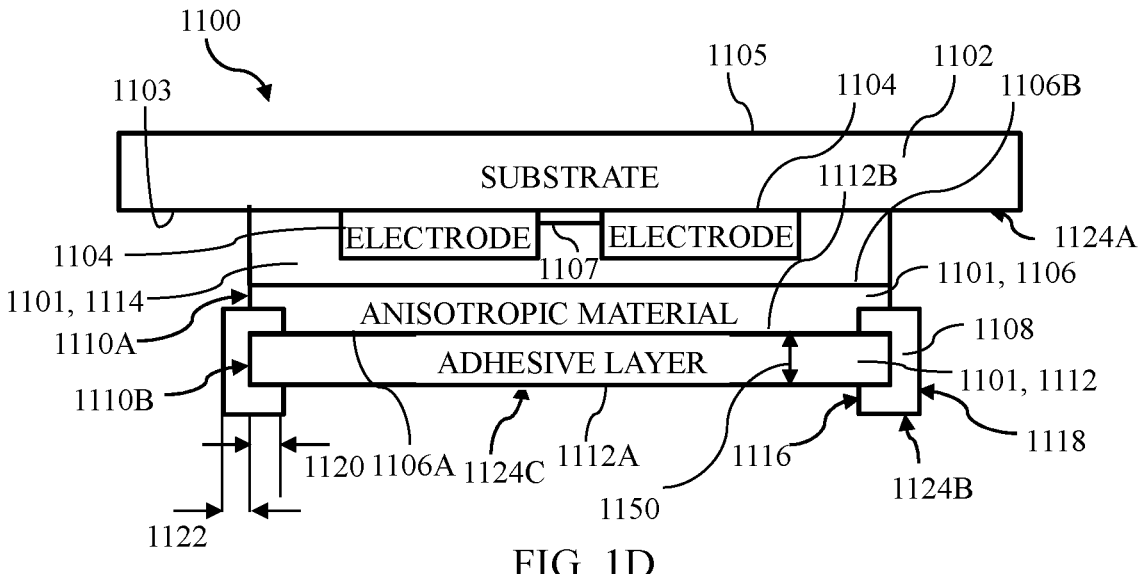

Transducer Apparatuses Used to Apply TTFields to a Subject's Body for Treating One or More Cancers FIGS. 1A-1D depict example transducers 1100 with a non-conductive border surrounding a conductive material layer of the transducer 1100. FIG. 1A is a bottom view showing the front face (skin-facing side) of the transducer 1100, and FIGS. 1B-1D are three examples of a side cross-sectional view of the transducer 1100 (taken at the cross-sections 11B-11B', 11C-11C', 11D-11D', respectively, FIG. 1A).

Figure 2A:
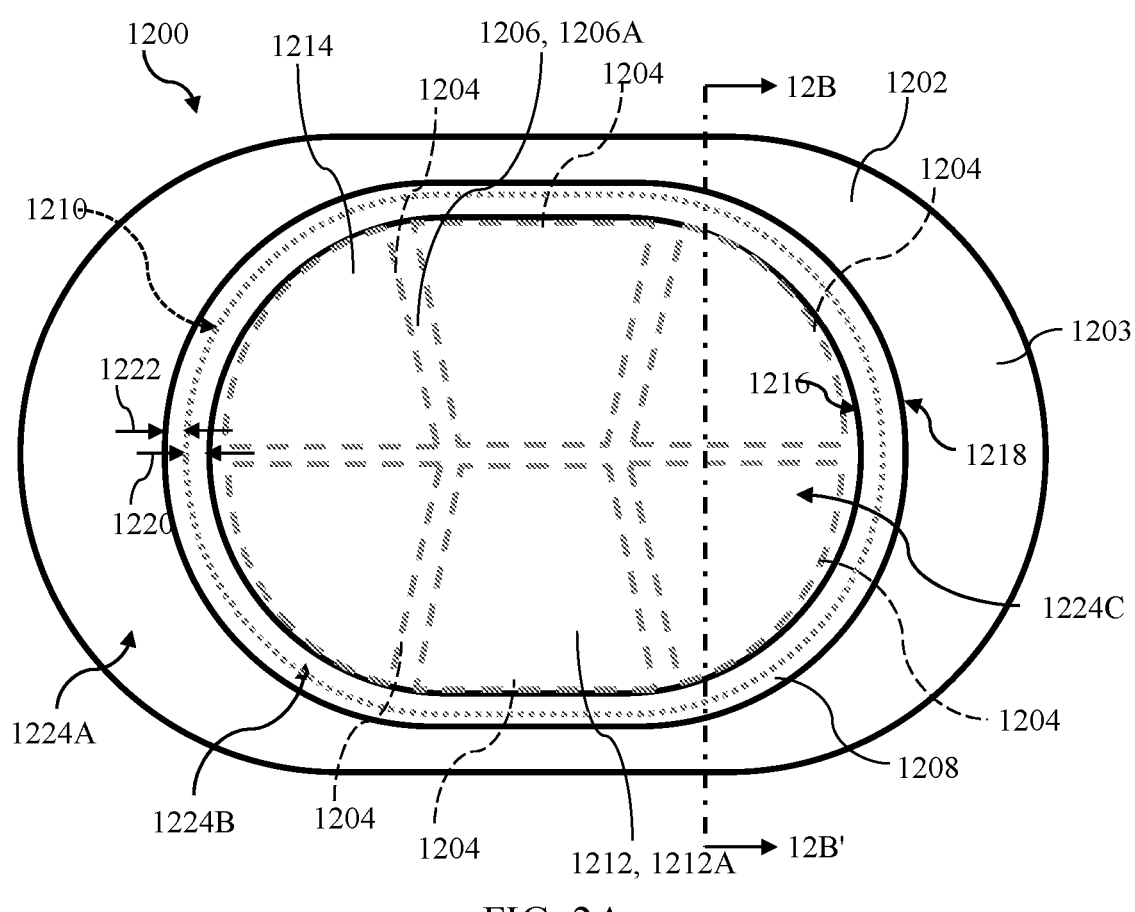
FIGS. 2A and 2B depict another example transducer with a non-conductive border.
Figure 2B:
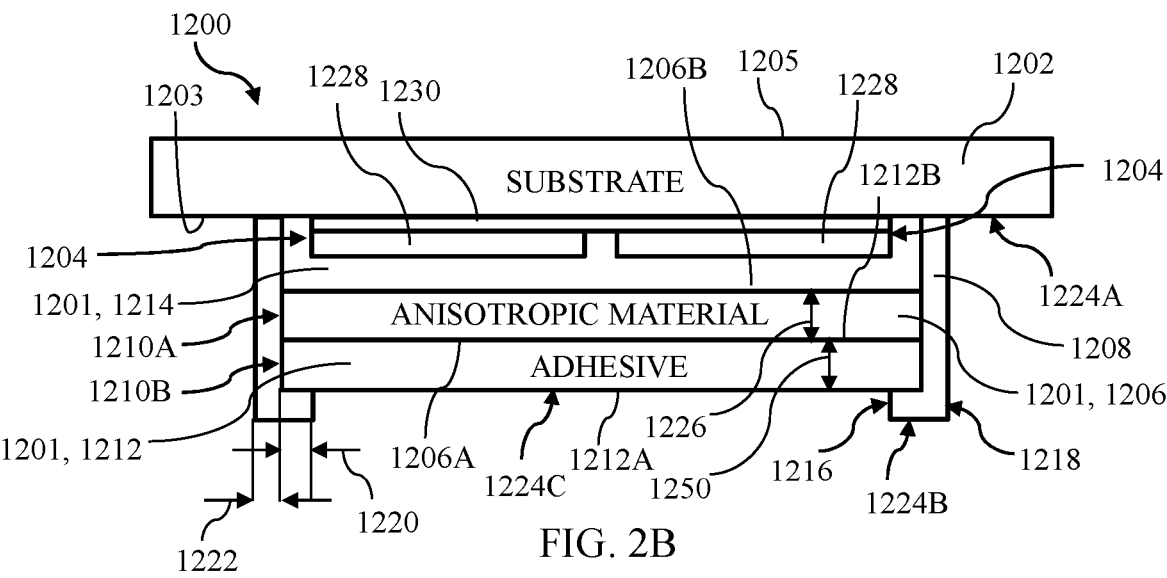

FIGS. 2A and 2B depict another example transducer 1200 with a non-conductive border surrounding a conductive material layer of the transducer 1200. FIG. 2A is a bottom view showing the front face of the transducer 1200, and FIG. 2B is a side cross-sectional view of the transducer 1200 (taken at the cross-sections 12B-12B', FIG. 2A).

Figure 3A:
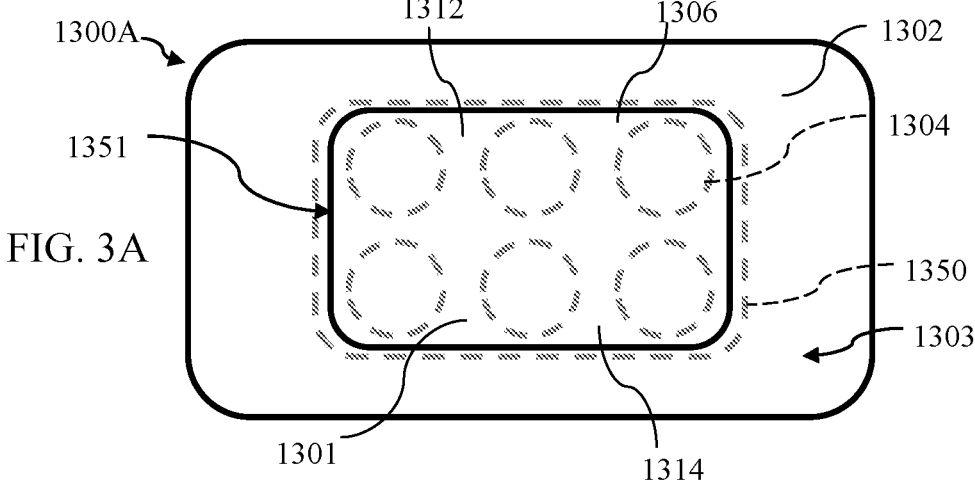
Figure 3B:
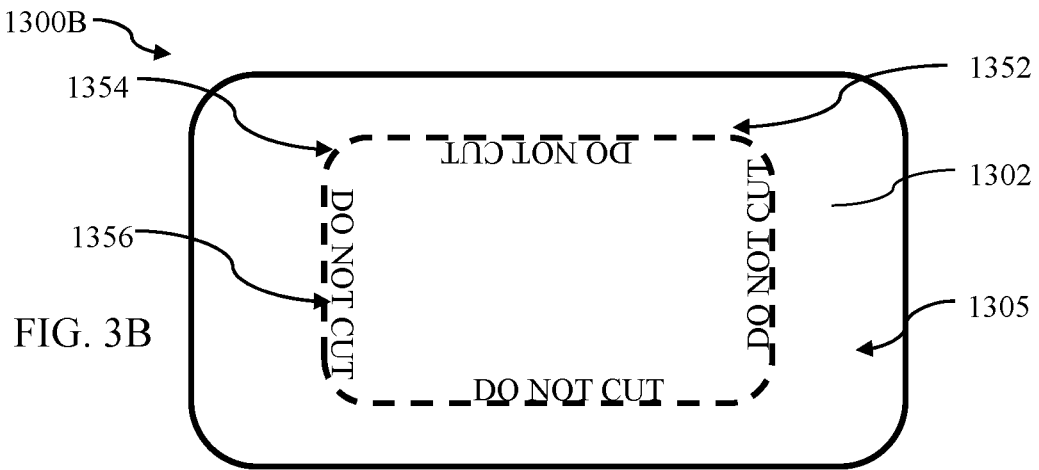

FIGS. 3A-3D depict example transducers 1300A-D with a visual indicator. FIG. 3A is a bottom view showing the front face of a transducer 1300A. FIGS. 3B-3D are top views showing the back face of different transducers 1300B-D, each of which may have the same bottom view as transducer 1300A.

Figure 4A:
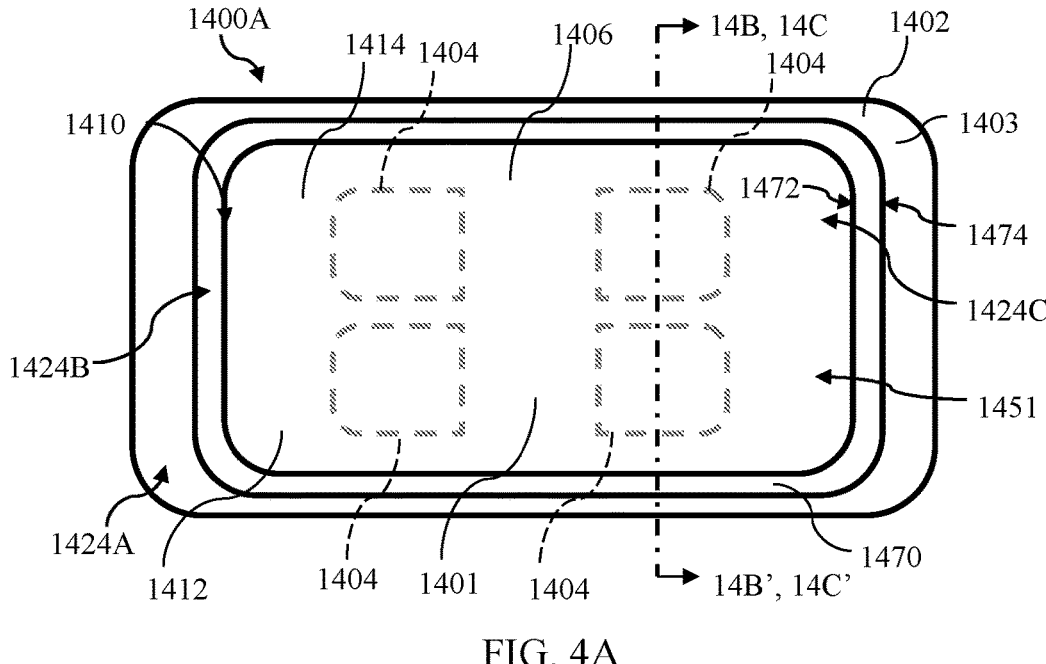
FIGS. 4A-4C depict example transducers with a cut-resistant material layer.
Figure 4B:
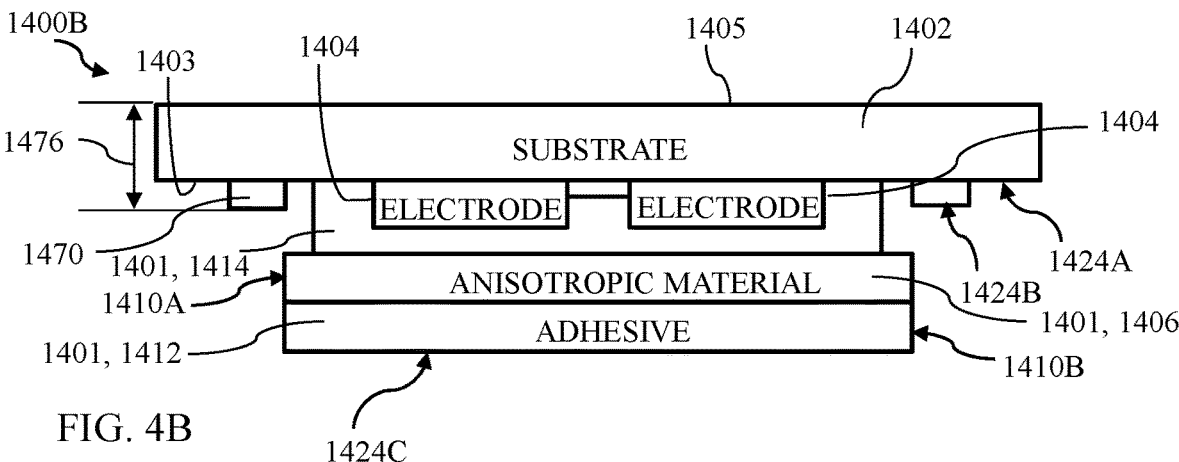
Figure 4C:
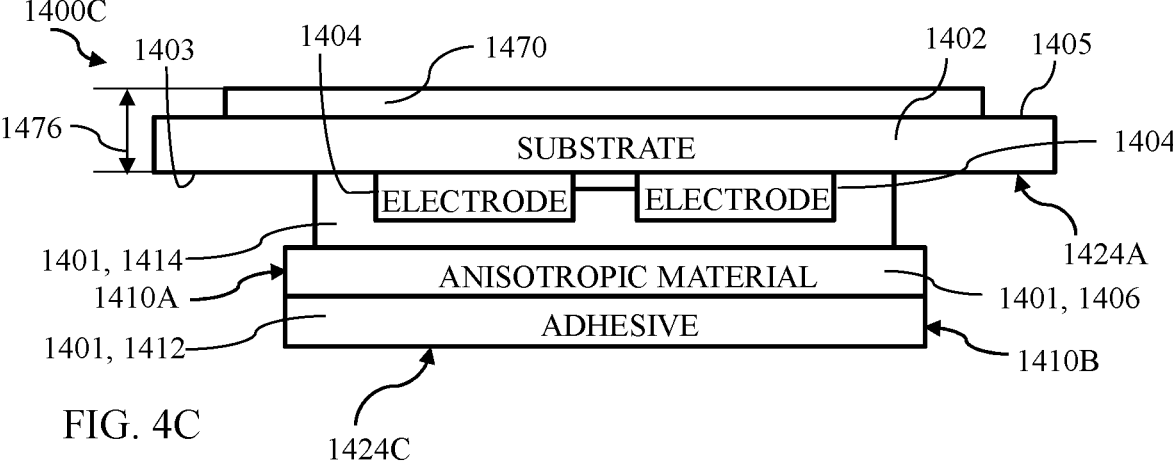

FIGS. 4A-4C depict example transducers 1400A-C with a cut-resistant material layer. FIG. 4A is a bottom view showing the front face of a transducer 1400A. FIGS. 4B and 4C are side cross-sectional views of different transducers 1400B and 1400C (taken at the cross-sections 14B-14B', 14C-14C', FIG. 4A). The transducer 1400B of FIG. 4B may have the same bottom view as transducer 1400A.

Each transducer (1100, 1200, 1300A-D, 1400A-C) of FIGS. 1A-4C is capable of delivering tumor treating fields to a subject's body.

In FIGS. 1A-4C, the transducer (1100, 1200, 1300A-D, 1400A-C) includes a substrate (1102, 1202, 1302, 1402) and at least one electrode element (1104, 1204, 1304, 1404) coupled to the substrate (1102, 1202, 1302, 1402), and a layer of anisotropic material (1106, 1206, 1306, 1406) coupled to the at least one electrode element (1104, 1204, 1304, 1404). The substrate (1102, 1202, 1302, 1402) has a front face (1103, 1203, 1303, 1403) and a back face (1105, 1205, 1305, 1405), and the electrode element(s) (1104, 1204, 1304, 1404) are located on a side of the front face (1103, 1203, 1303, 1403) of the substrate (1102, 1202, 1302, 1402). As illustrated, the electrode element(s) (1104, 1204, 1304, 1404) are located between the substrate (1102, 1202, 1302, 1402) and the layer of anisotropic material (1106, 1206, 1306, 1406). As shown in FIGS. 1A-2B, the layer of anisotropic material (1106, 1206) has a front face (1106A, 1206A) and a back face (1106B, 1206B), with the back face facing the electrode element(s) (1104, 1204)

The transducer (1100, 1200, 1300A-D, 1400A-C) of each of FIGS. 1A-4C may be affixed to the subject's body via the substrate (1102, 1202, 1302, 1402). Suitable materials for the substrate (1102, 1202, 1302, 1402) may include, for example, cloth, foam, flexible plastic, and/or a conductive medical gel or adhesive.

In FIGS. 1A-4C, the transducers (1100, 1200, 1300A-D, 1400A-C) comprise arrays of substantially flat electrode element(s) (1104, 1204, 1304, 1404). For each figure, the array of electrode elements (1104, 1204, 1304, 1404) may be capacitively coupled. In one example, as shown in FIGS. 1B, 1C and 1D, the electrode elements 1104 are ceramic electrode elements coupled to each other via conductive wiring 1107. When viewed in a direction perpendicular to its face, the ceramic electrode elements may be circular shaped (e.g., 1304 in FIG. 3A) or non-circular shaped (e.g., 1104 in FIG. 1A). In another example, as shown in FIG. 2B, the electrode elements 1204 are non-ceramic dielectric materials positioned over a plurality of flat conductors. When viewed in a direction perpendicular to its face, the non-ceramic electrode elements may take any desired shape (e.g., elements 1204 in FIG. 2A). Examples of non-ceramic dielectric materials positioned over flat conductors include polymer films 1228 disposed over pads on a printed circuit board 1230 or over substantially planar pieces of metal. Preferably, such polymer films have a high dielectric constant, for example having a dielectric constant greater than 10. In other embodiments, the array of electrode elements (1104, 1204, 1304, 1404) are not capacitively coupled, and there is no dielectric material associated with the electrode elements (1104, 1204, 1304, 1404). The electrode elements (1104, 1204, 1304, 1404) may take any of these forms without departing from the scope of the present disclosure.

The transducer (1100, 1200, 1300A-D, 1400A-C) also includes at least one conductive material layer (1101, 1201, 1301, 1401). In some embodiments, the conductive material layer (1101, 1201, 1301, 1401) may be a layer of anisotropic material (1106, 1206, 1306, 1406) coupled to the at least one electrode element (1104, 1204, 1304, 1404). As shown in FIGS. 1A-4C, the electrode element(s) (1104, 1204, 1304, 1404) may be located between the substrate (1102, 1202, 1302, 1402) and the layer of anisotropic material (1106, 1206, 1306, 1406). As shown in FIGS. 1A-2B, the layer of anisotropic material (1106, 1206) has a front face (1106A, 1206A) and a back face (1106B, 1206B), with the back face facing the electrode element(s) (1104, 1204). In some embodiments, the conductive material layer (1101, 1201, 1301, 1401) may be a hydrogel layer or an electrically conductive adhesive layer electrically coupled to the at least one electrode element (1104, 1204, 1304, 1404). The hydrogel layer or electrically conductive adhesive layer may be located on an opposite side of the electrode element(s) (1104, 1204, 1304, 1404) from the substrate (1102, 1202, 1302, 1402). The hydrogel layer or electrically conductive adhesive layer may be a conductive skin contact adhesive layer (1112, 1212, 1312, 1412). As shown in FIGS. 1A-2B, the electrically conductive skin contact adhesive layer (1112, 1212) has a front face (1112A, 1212A) and a back face (1112B, 1212B), with the back face facing the electrode element(s) (1104, 1204). As illustrated, when a layer of anisotropic material (1106, 1206, 1306, 1406) is present in the transducer (1100, 1200, 1300, 1400), the layer of anisotropic material (1106, 1206, 1306, 1406) is located between the electrode element(s) (1104, 1204, 1304, 1404) and the electrically conductive skin contact adhesive layer (1112, 1212, 1312, 1412). Alternatively, or additionally, a hydrogel layer or electrically conductive adhesive layer may function as an upper adhesive layer (1114, 1214, 1314, 1414) located between the electrode element(s) (1104, 1204, 1304, 1404) and the layer of anisotropic material (1106, 1206, 1306, 1406). In some embodiments, the layer of anisotropic material (1106, 1206, 1306, 1406) is sandwiched between two layers of hydrogel, or sandwiched between two layers of electrically conductive adhesive, or sandwiched between one layer of each.

The layer of anisotropic material (1106, 1206, 1306, 1406) of FIGS. 1A-4C may be any conductive layer having different thermal and/or electrical conductivities in a direction perpendicular to the front face (1103, 1203, 1303, 1403) of the substrate (1102, 1202, 1302, 1402) than in directions that are parallel to the front face (1103, 1203, 1303, 1403). The layer of anisotropic material may be anisotropic with respect to electrical conductivity properties, anisotropic with respect to thermal properties, or both. This allows the layer of anisotropic material to spread out current and/or heat over a larger surface area. In each case, this lowers the temperature of hot spots and raises the temperature of cooler regions when a given AC voltage is applied to the array of electrode elements. Accordingly, the current can be increased without exceeding a safety temperature threshold at any point on the subject's skin. The layer of anisotropic material may be a sheet of pyrolytic graphite, graphitized polymer film, a graphite foil made from compressed high purity exfoliated mineral graphite, or some other material. Other details regarding the layer of anisotropic material and properties thereof are described in U.S. Provisional Patent Application Nos. 63/230,438 and 63/275,841, which are hereby incorporated by reference in the present disclosure.

The electrically conductive skin contact adhesive layer (1112, 1212, 1312, 1412) and/or the electrically conductive upper adhesive layer (1114, 1214, 1314, 1414) may be a composite adhesive layer. For example, the electrically conductive adhesive layer (1112, 1212, 1312, 1412; or 1114, 1214, 1314, 1414) may comprise a plurality of electrically conductive particles embedded at least partially within an adhesive matrix material. The electrically conductive particles may provide enhanced electrical conductivity in the x-y plane of the adhesive layer. The electrically conductive particles may include carbon granules, carbon flakes, graphite powder, carbon black powder, carbon nanoparticles, carbon nanotubes, and the like. The electrically conductive particles may include electrically conductive fibers, such as carbon fibers, or carbon wires or nanowires. The electrically conductive particles may comprise graphite. The plurality of electrically conductive particles may comprise a sheet of fibers embedded in the adhesive matrix material. The sheet of fibers may be in the form of a mesh layer that can be cut to any desired shape, which becomes the areal footprint of the conductive material layer (1101, 1201, 1301, 1401). The electrically conductive fibers may be oriented such that the longitudinal axes of each of the fibers is substantially (e.g., within 20 degrees, or within 10 degrees) parallel to the x-y plane of the adhesive layer (1112, 1212, 1312, 1412; or 1114, 1214, 1314, 1414). In some embodiments, the electrically conductive fibers may provide enhanced electrical conductivity in the x-y plane of the adhesive layer. The adhesive matrix material may comprise any suitable polymer, for example, the adhesive matrix material may comprise an acrylic polymer matrix material or a silicone polymer matrix material. The conductive adhesive layer (1112, 1212, 1312, 1412; or 1114, 1214, 1314, 1414) may comprise a medical grade adhesive that requires no hydrogel or Ag/AgCl to get a signal, sold under the trademark FLEXcon® OMNI-WAVE™ (available from FLEXcon located in Spencer, Massachusetts, USA).

In some embodiments, the electrically conductive adhesive layer (1112, 1212, 1312, 1412; or 1114, 1214, 1314, 1414) may not include a plurality of electrically conductive particles that provide enhanced electrical/heat conductivity in the x-y plane of the adhesive layer. In other embodiments, the layer of anisotropic material may not be present in the transducer (1100, 1200, 1300, 1400), such that the one or more electrically conductive adhesive layers (1112, 1212, 1312, 1412; or 1114, 1214, 1314, 1414) are the only conductive material layer(s) (1101, 1201, 1301, 1401).

The one or more conductive material layer(s) (1101, 1201, 1301, 1401), which includes the layer of anisotropic material (1106, 1206, 1306, 1406), the electrically conductive skin contact adhesive layer (1112, 1212, 1312, 1412), or the electrically conductive upper adhesive layer (1114, 1214, 1314, 1414), or a combination thereof, may take any desired shape. For example, as shown in FIGS. 1A and 4A, a perimeter ring (1110, 1410) of the conductive material layer (1101, 1401), which represents the outer perimeter (1110A, 1410A) of the layer of anisotropic material (1106, 1406) and the outer perimeter (1110B, 1410B) of the electrically conductive skin contact adhesive layer (1112, 1412), may have a substantially square or rectangular shape, or substantially square or rectangular shape with rounded corners. As another example, as shown in FIG. 2A, an outer perimeter 1210 of the conductive material layer 1201, which represents the outer perimeter 1210A of the layer of anisotropic material 1206 and the outer perimeter 1210B of the electrically conductive skin contact adhesive layer 1212 may have a circular, oval, ovoid, ovaloid, or elliptical shape. In FIGS. 1A, 2A, and 4A, the outer perimeter (1110, 1210, 1410) of the layer of anisotropic material (1106, 1206, 1406) and the electrically conductive skin contact adhesive layer (1112, 1212, 1412) defines an areal footprint of the conductive material layer(s) (1101, 1201, 1301, 1401). Although the outer perimeter (1110, 1210, 1410) in FIGS. 1A, 2A, and 4A represents the outer perimeters (1110A/B, 1210A/B, 1410A/B) of both the layer of anisotropic material (1106, 1206,

1406) and the electrically conductive skin contact adhesive layer (1112, 1212, 1412), in other embodiments the outer perimeter (1110, 1210, 1410) may correspond to only one of the layer of anisotropic material (1106, 1206, 1406) or the electrically conductive adhesive layer(s) (1112, 1212, 1412; 1114, 1214, 1314, 1414). This may be the case where the outer perimeter (1110A, 1210A, 1410A) of the layer of anisotropic material (1106, 1206, 1406) is different from the outer perimeter (1110B, 1210B, 1410B) of the electrically conductive adhesive layer(s) (1112, 1212, 1412; 1114, 1214, 1314, 1414).

Turning to FIGS. 1A-2B, the transducer 1100, 1200 further includes a non-conductive material border (1108, 1208) disposed over the outer perimeter (1110, 1210) of the conductive material layer(s) (1101, 1201). That is, the transducer 1100, 1200 includes the non-conductive material border (1108, 1208) disposed over the outer perimeter (1110A, 1210A) of the layer of anisotropic material (1106, 1206) and/or over the outer perimeter (1110B, 1210B) of the electrically conductive adhesive layer(s) (1112, 1212; 1114, 1214). The non-conductive material border (1108, 1208) is electrically non-conductive. As illustrated in FIGS. 1A and 2A, the non-conductive material border (1108, 1208) may be generally ring-shaped or annular shaped, having an inner edge (1116, 1216) and an outer edge (1118, 1218). When viewed in a direction perpendicular to the front face (1106A, 1206A) of the layer of anisotropic material (1106, 1206), the inner edge (1116, 1216) overlaps a portion of the front face (1106A, 1206A) of the layer of anisotropic material (1106, 1206), and the outer edge (1118, 1218) extends outside the outer perimeter (1110A, 1210A) of the layer of anisotropic material (1106, 1206). In an example, the inner edge (1116, 1216) of the non-conductive material border (1108, 1208) overlaps the front face (1106A, 1206A) of the layer of anisotropic material (1106, 1206) along an entire length of the inner edge (1116, 1216), and the outer edge (1118, 1218) of the non-conductive material border (1108, 1208) extends outside the outer perimeter (1110A, 1210A) of the layer of anisotropic material (1106, 1206) along an entire length of the non-conductive material border (1108, 1208), such that all of the outer perimeter (1110A, 1210A) of the layer of anisotropic material (1106, 1206) is covered by the non-conductive material border (1108, 1208). The inner edge (1116, 1216) of the non-conductive material border (1108, 1208) may extend a distance (1120, 1220) of at least 1 mm, at least 2 mm, at least 3 mm, or more, inward from the outer perimeter (1110A, 1210A) of the layer of anisotropic material (1106, 1206). The outer edge (1118, 1218) of the non-conductive material border (1108, 1208) may extend a distance (1122, 1222) of at least 1 mm, at least 2 mm, at least 3 mm, or more, outside of the outer perimeter (1110A, 1210A) of the layer of anisotropic material (1106, 1206). As illustrated in FIGS. 1A-2B, the inner edge (1116, 1216) and outer edge (1118, 1218) of the non-conductive material border (1108, 1208) may have a similar overlapping arrangement with respect to the front face (e.g., 1112A, 1212A) and to the outer perimeter (e.g., 1110B, 1210B) of the electrically conductive adhesive layer(s) (1112, 1212; 1114, 1214) as described at length above with respect to the front face (1106A, 1206A) and outer perimeter (1110A, 1210A) of the layer of anisotropic material (1106, 1206).

In an example, the non-conductive material border (1108, 1208) may be, or may comprise, a non-conductive adhesive. The non-conductive adhesive may be a medical adhesive. The non-conductive adhesive may be sprayed onto or otherwise applied to the rest of the transducer (1100, 1200) to form the non-conductive material border (1108, 1208). As described above, the non-conductive adhesive may be applied such that all of the outer perimeter (1110, 1210) of the conductive material layer (1101, 1201) (e.g., all of the outer perimeter (1110A, 1110B) of the layer of anisotropic material (1106, 1206) and/or all of the outer perimeter (1110B, 1210B) of the electrically conductive adhesive layer(s) (1112, 1212; 1114, 1214)) is covered by the non-conductive adhesive. In another embodiment, the non-conductive adhesive may be applied only outside of the outer perimeter (1110, 1210) of the conductive material layer (1101, 1201), for example, starting at the outer perimeter (1110, 1210) and extending outside of the outer perimeter (1110, 1210) to form an adhesive "skirt"; or starting outside the outer perimeter (1110, 1210) and extending further outside of the outer perimeter (1110, 1210) to form an adhesive "skirt". The latter approach may be advantageous compared to relying on the area of bandage outside of the outer perimeter (1110, 1210), particularly if the adhesive used for the "skirt" is less irritating on the skin than the bandage adhesive. The same adhesive "skirt" may be achieved in practice by coating a layer (or area with a central void) of non-conductive adhesive over a portion of the front face (1103, 1203) of the substrate bandage (1102, 1202) prior to applying the electrode assembly comprising the conductive material layer (1101, 1201) onto the substrate (1102, 1202). In this method of construction, the layer (or area with a central void) of non-conductive adhesive extends out from beneath the layer of anisotropic material (1106, 1206), extending beyond the outer perimeter (1110, 1210) thereby forming the adhesive "skirt".

In another example, the non-conductive material border (1108, 1208) may comprise a tape, bandage, or plaster. In particular, the non-conductive material border (1108, 1208) may comprise an electrical tape or a non-conductive medical tape. The non-conductive tape or bandage may be applied as an "o-ring" to seal the outer edge of the layer of anisotropic material (1106, 1206) and/or the electrically conductive adhesive layer(s) (1112, 1212; 1114, 1214). In an embodiment, for example, as shown in FIGS. 1B and 2B, the non-conductive tape or bandage may adhere to the front face (1106A, 1206A), or on the front facing side, of the layer of anisotropic material (1106, 1206) within the outer perimeter (1110A, 1210A) of the layer of anisotropic material (1106, 1206) and also adhere to the substrate (1102, 1202) outside of the outer perimeter (1110A, 1210A) of the layer of anisotropic material (1106, 1206). In another embodiment, for example, as shown in FIG. 1C, the non-conductive tape or bandage may adhere to the front face (1106A), or on the front facing side, of the layer of anisotropic material 1106 within the outer perimeter (1110A) of the layer of anisotropic material 1106 and also be folded to adhere to the back face (1106B), or on the back facing side, of the layer of anisotropic material 1106. In another embodiment, for example, as shown in FIG. 1D, the non-conductive tape or bandage may adhere to the front face (1112A) of the electrically conductive skin contact adhesive layer (1112) within the outer perimeter (1110B) of the electrically conductive skin contact adhesive layer (1112) and also be folded to adhere to the back face (1112B) of the electrically conductive skin contact adhesive layer (1112). In some embodiments, a one-sided or two-sided non-conductive tape, band-aid or plaster may be added around the perimeter ring (1110, 1410).

The non-conductive material border (1108, 1208) may prevent or protect against a short circuit occurring between the transducer 1100, 1200 and an adjacent transducer positioned on a subject's body, even if one or both of the transducers have been cut. The non-conductive material border (1108, 1208) is a border defined by a physical barrier (i.e., the non-conductive material). The non-conductive material border (1108, 1208) surrounds an areal exclusion zone of the transducer (1100, 1200) containing at least the areal footprint of the layer of anisotropic material (1106, 1206). The non-conductive material border (1108, 1208) may seal the outer edge of the layer of anisotropic material (1106, 1206) from electrical contact with other transducers in its vicinity.

In FIGS. 1A-2B, the transducer (1100, 1200) may further include one or more electrically conductive adhesive layers. For example, the transducer (1100, 1200) may include an electrically conductive adhesive layer (1112, 1212) located on the front face (1106A, 1206A) of the layer of anisotropic material between the layer of anisotropic material (1106, 1206) and the front face (1124B, 1224B) of the non-conductive material border (1108, 1208). Additionally, or alternatively, the transducer (1100, 1200) may include the electrically conductive upper adhesive layer (1114, 1214) located between the at least one electrode element (1104, 1204) and the back face (1106B, 1206B) of the layer of anisotropic material (1106, 1206). The upper adhesive layer (1114, 1214) may extend from the substrate (1102, 1202) to the layer of anisotropic material (1106, 1206). Alternatively, the upper adhesive layer (1114, 1214) may simply coat the front face of the at least one electrode element (1104, 1204) facing the layer of anisotropic material (1106, 1206). The transducers of FIGS. 3A-4C may similarly include an electrically conductive adhesive layer (1312, 1412) located on the front face of the layer of anisotropic material (1306, 1406), and/or an electrically conductive upper adhesive layer (for example, 1414) located between electrode element (s) (1304, 1404) and the back face of the layer of anisotropic material (1306, 1406).

In an example, as shown in FIGS. 1B, 1C, and 2B, the non-conductive material border (1108, 1208) covers a full thickness (1126, 1226) of the layer of anisotropic material (1106, 1206) in the direction perpendicular to the front face (1106A, 1206A) of the layer of anisotropic material (1106, 1206). As shown in FIGS. 1B-1D and 2B, the non-conductive material border (1108, 1208) may cover a full thickness (1150, 1250) of the electrically conductive skin contact adhesive layer (1112, 1212) in the direction perpendicular to the front face (1112A, 1212A) of the electrically conductive skin contact adhesive layer (1112, 1212). As shown in FIG. 1B, the non-conductive material border (1108) may cover a full thickness of the electrically conductive upper adhesive layer 1114 in the direction perpendicular to the front face 103 of the substrate 1102. In addition, as shown in FIGS. 1B and 2B, the non-conductive material border (1108, 1208) may be adhered to the front face (1103, 1203) of the substrate (1102, 1202). As such, the non-conductive material border (1108, 1208) may extend from the front face (1103, 1203) of the substrate (1102, 1202) to the very front of the transducer (1100, 1200), thereby covering the full thickness of all conductive material layers (1101, 1201). As constructed, transducers 1100 and 1200 may present exposed surfaces facing in the forward-facing direction. In transducers 1100 and 1200, the forward-facing surfaces of the substrate (1102, 1202), cut-resistant material layer (1170, 1270), and conductive adhesive layer (1112, 1212) are surfaces 1124A/1224A, 1124B/1224B and 1124C/1224C, respectively. The dimensions of various components of the transducer (1100, 1200) in FIGS. 1B, 1C, and 2B are not shown to scale, and the transducer (1100, 1200) may be substantially flat such that surfaces (1124A-C, 1224A-C) of multiple components of the transducer (1100, 1200) contact the subject's body upon placement of the transducer (1100, 1200) on the subject's body.

The non-conductive material border (1108, 1208) may provide a third level of separation between the conductive material layer(s) (1101, 1201) of the transducer (1100, 1200) and a conductive portion of an adjacent transducer, in addition to (1) a recommended relative placement of the transducers on the subject's body; and (2) the substrate (1102, 1202) located on the back side of the conductive material layer (1101, 1201).

Turning to FIGS. 3A-3D, the transducer 1300A-D further includes a visual indicator 1352 that is visible from a side of the back face 1305 of the substrate 1302. The visual indicator 1352 indicates a border 1350 surrounding an areal exclusion zone 1351 of the transducer 1300A, the areal exclusion zone 1351 containing at least an areal footprint of the conductive material layer(s) 1301 (e.g., the layer of anisotropic material 1306 and/or the electrically conductive adhesive layer(s) 1312, 1314). The border 1350 surrounding the areal exclusion zone 1351 may extend at least 1 mm outside of the areal footprint of the conductive material layer(s) 1301 (e.g., the layer of anisotropic material 1306 and/or the electrically conductive adhesive layer(s) 1312, 1314) on all sides. The border 1350 may have a circular, oval, ovoid, ovaloid, or elliptical shape, or substantially square or rectangular shape, or substantially square or rectangular shape with rounded corners.

The visual indicator 1352 provides a visual clue (with coloring/markings and/or via a difference in thickness of the substrate 1302) on the back face 1305 of the substrate 1302 to deter a user from cutting a portion of the transducer 1300 having the areal exclusion zone 1351. One or more of the different types of visual indicators 1352 described below may be included in the same transducer.

In FIGS. 3B and 3C, the visual indicator 1352 includes coloring and/or markings to identify the border (1350 of FIG. 3A) surrounding the areal exclusion zone. As shown in FIG. 3B, the visual indicator 1352 may include at least one solid, dashed, ticked, or otherwise patterned line 1354 on the back face 1305 of the substrate 1302, or visible from the back side of the substrate 1302, tracing the border surrounding the areal exclusion zone. As shown in FIG. 3B, the visual indicator 1352 may include text 356 on the substrate 1302. The text 1356 may identify a region in which to cut the substrate 1302, a region where not to cut the substrate 1302, or both. As shown in FIG. 3C, the visual indicator 1352 may include an area 1358 of the substrate 1302 located inside the border surrounding the areal exclusion zone having a different color and/or pattern than an area of the substrate 1302 located outside the border surrounding the areal exclusion zone. For example, the area 1358 located inside the border may have red ink printed thereon to indicate that the substrate 1302/transducer 1300C are not to be cut in this zone.

In FIG. 3D, the visual indicator 1352 includes a non-printed type of visual indication. As shown in FIG. 3D, the visual indicator 1352 may include a visually identifiable raised portion 1360 of the surface of the substrate 1302 along the border (1350 of FIG. 3A) surrounding the areal exclusion zone. The visually identifiable raised portion 1360 may be due to the presence of an additional material layer coupled to the substrate 1302. The additional material layer may increase a thickness of the substrate 1302 in the direction perpendicular to the back face 1305 of the substrate 1302. The additional material layer may be the same or a different color than the substrate 1302. In an example, the visually identifiable raised portion 1360 may be due to the presence of a cut-resistant material layer coupled to the substrate 1302, described in detail below.

Turning to FIGS. 4A-4C, the transducer 1400A-C further includes a cut-resistant material layer 1470 coupled to the substrate 1402. The cut-resistant material layer 1470 defines a border surrounding an areal exclusion zone 1451 of the transducer (shown in FIG. 4A), the areal exclusion zone 1451 containing at least an areal footprint of the conductive material layer(s) 1401 (e.g., the layer of anisotropic material 1406 and/or the electrically conductive adhesive layer(s) 1412, 1414). The border surrounding the areal exclusion zone 1451 may extend at least 1 mm outside of the areal footprint of the conductive material layer(s) 1401 (e.g., the layer of anisotropic material 1406 and/or the electrically conductive adhesive layer(s) 1412, 1414) on all sides.

The cut-resistant material layer 1470 is configured to prevent, deter, or reduce the amount by which a user can cut through the combined substrate 1402 and cut-resistant material layer 1470 with scissors or the like. As such, the cut-resistant material layer 1470 is placed in an area where it is undesirable to cut the transducer 1400 and provides physical resistance to such cutting. The cut-resistant material layer 1470 may be made from a thermosetting or thermoplastic polymeric material, a reinforced polymeric material, a reinforced fabric (e.g., containing Kevlar®, available from DuPont de Nemours, Inc., Wilmington, DE, USA), or a combination thereof. The cut-resistant material layer 1470 may be coupled to the substrate 1402 via adhesive. As shown in FIGS. 4B and 4C, a combined thickness 1476 of the substrate 1402 and the cut-resistant material layer 1470 may be greater than 500 μm, or greater than 800 μm, or greater than 1000 μm, or greater than 1,200 μm, in the direction perpendicular to the front face 1403 of the substrate 1402.

Various different configurations of the cut-resistant material layer 1470 may be used. In an example, as shown in FIG. 4B, the cut-resistant material layer 1470 is coupled to the front face 1403 of the substrate 1402. In this configuration, the cut-resistant material layer 1470 may be used in combination with a visual indicator (e.g., 1352 of FIGS. 3B-3D) on the back face 1405 of the substrate 1402 to indicate the border defined by the cut-resistant material layer 1470. As shown in FIG. 4A, the cut-resistant material layer 1470 may not overlap the entirety of the areal exclusion zone 1451. That is, the cut-resistant material layer 1470 may include an outer edge 1474 that defines the border surrounding the areal exclusion zone 1451 and an inner edge 1472 that defines an opening within the cut-resistant material layer 1470. That is, as shown in FIGS. 4A and 4B, the cut-resistant material layer 1470 may take the form of a continuous strip that follows the border of the areal exclusion zone 1451. In another example (e.g., in FIG. 4C), the cut-resistant material layer 1470 is coupled to the back face 1405 of the substrate 1402. In this example, the cut-resistant material layer 1470 may overlap the entirety of the areal exclusion zone 1451, the cut-resistant material layer 1470 having just an outer edge.

For the transducer 1400B, the forward-facing surfaces of the substrate 1402, cut-resistant material layer 1470, and conductive adhesive layer 1412 are surfaces 1424A, 1424B and 1424C, respectively. For the transducer 1400C, the forward-facing surfaces of the substrate 1402 and conductive adhesive layer 1412 are surfaces 1424A and 1424C, respectively. The dimensions of various components of the transducer (1400B, 1400C) in FIGS. 4B and 4C are not shown to scale, and the transducer (1400B, 1400C) may be substantially flat such that surfaces (1424A-C for transducer 1400B, and 1424A and 1424C for transducer 1400C) of multiple components of the transducer (1400B, 1400C) contact the subject's body upon placement of the transducer (1400B, 1400C) on the subject's body.

In some embodiments, the non-conductive material border (1108, 1208) or the surrounding cut-resistant material layer 1470 may help with mechanical stability. For example, with respect to a tendency for the layer of anisotropic material (or combined layers of anisotropic material and conductive adhesive layers) to delaminate in the center, the non-conductive material border (1108, 1208) or the surrounding cut-resistant material layer 1470 may help with reducing, minimizing, or preventing delamination of the layer of anisotropic material.

Figure 5:
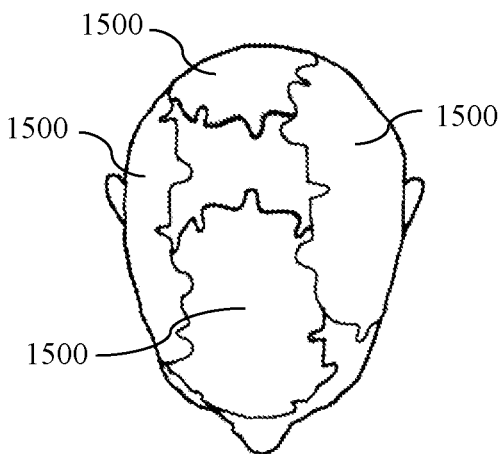
FIG. 5 depicts an example arrangement of transducers located on a subject's head.

FIG. 5 depicts an example arrangement of transducers 1500 located on a subject's head. FIG. 5 depicts an example of a subject's head on which transducers 1500 are placed in varying positions and/or orientations. Such arrangements of transducers 1500 on a subject's head are capable of applying TTFields to a tumor in a region of the subject's brain. The transducers 1500 illustrated in FIG. 5 have different shapes than the transducers 1100, 1200 shown in the embodiments of FIGS. 1A and 2A and the transducers 2200A-D, 2400, 2500A-B shown in the embodiments of FIGS. 6, 8A, 9A, and 9B. In particular, the transducers 1500 include tabs and recesses along an outer perimeter of the transducer substrate, giving the outer perimeter a scalloped edge. However, transducers having straight or more uniformly curved edges on the outer perimeter of the transducer substrate, such as shown in FIGS. 1A, 2A, 6, 8A, 9A, and 9B, may be arranged on the subject's head in a similar manner as the transducers 1500 of FIG. 5. In addition, the substrate (1102, 1202, 2202A-D, 2402, 2502) of FIGS. 1A-2B, 6, and 8A-9B may, in other embodiments, have a scalloped outer perimeter as shown in FIG. 5.

As illustrated, some of the adjacent transducers 1500 may overlap each other on the subject's head. A user may cut one or more portions of the transducer(s) 1500 to fit the transducers 1500 together, to fit the transducers 1500 around anatomical features, or simply to reduce the amount of adhesive touching the subject's body. The transducers 1500 may be equipped with one or more of the above-described protective borders, in the form of a non-conductive material border (e.g., FIGS. 1A-2B), a visual indicator (e.g., FIGS. 3A-3D), a cut-resistant material layer (e.g., FIGS. 4A-4C), or a combination of any two or more of these features. For transducers positioned on the head, or, indeed, for transducers positioned anywhere else on the body, these protective borders may provide an additional layer of protection against a short circuit (e.g., through a non-conductive material border), and/or deter or prevent a user from cutting an areal exclusion zone that would otherwise expose the conductive material layer. Additionally, a system including transducers 1500 may use one or more of the below described active detection processes, in the form of a conductive wire sensor (FIGS. 9A and 9B), a method for detecting a short circuit based on sensor measurements (FIGS. 10-12), or a combination of any two or more of these features. These active detection processes may alert a user to an improper configuration of one or more of the transducers 1500.

Methods to Detect an Improper Configuration of Transducers on a Subject's Body

Figure 6:
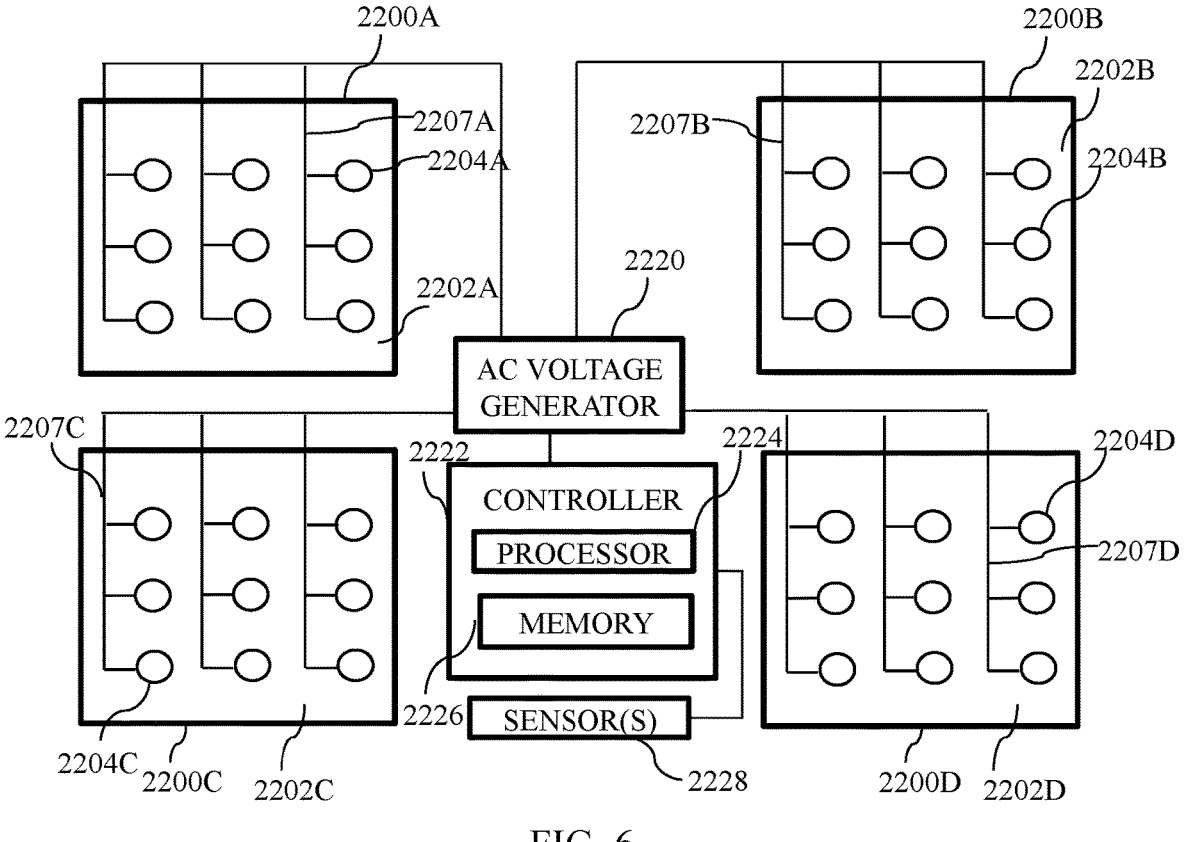
FIG. 6 depicts an example system having four transducers.

FIG. 6 depicts an example system having four transducers 2200A-D. The system may be used for delivering TTFields to a subject's body. Each transducer 2200A-D may include substantially flat electrode elements 2204A-D positioned on a substrate 2202A-D and electrically and physically connected (e.g., through conductive wiring 2207A-D). The substrates 2202A-D may include, for example, cloth, foam, flexible plastic, and/or conductive medical gel.

The transducers 2200A-D may be coupled to an AC voltage generator 2220 and a controller 2222 communicatively coupled to the AC voltage generator 2220. The controller 2222 may include a computer having one or more processors 2224 and memory 2226. The memory 2226 may store instructions that when executed by the one or more processors control the AC voltage generator 2220 to induce TTfields between a pair of the transducers 2200A-D and/or cause the computer to perform one or more methods disclosed herein. The controller 2222 may monitor operations performed by the AC voltage generator 2220 (e.g., via the processor(s) 2224) and store voltage and/or current values in memory 2226. One or more sensor(s) 2228 may be coupled to the controller 2222 for providing measurement values or other information to the controller 2222. In an example, the sensor(s) 2228 may include a conductive wire sensor (as described with reference to FIGS. 13A and 13B) provided on each of the transducers 2200A-D. In such embodiments, the voltage generator 2220 may supply a voltage to the wire of the conductive wire sensor. Additionally, or alternatively, the sensor(s) 2228 may be configured to collect other types of information (e.g., operational status, temperature values, etc.). The voltage values, current values, and other types of information may be stored in a log file in the memory 2226.

Figure 7:
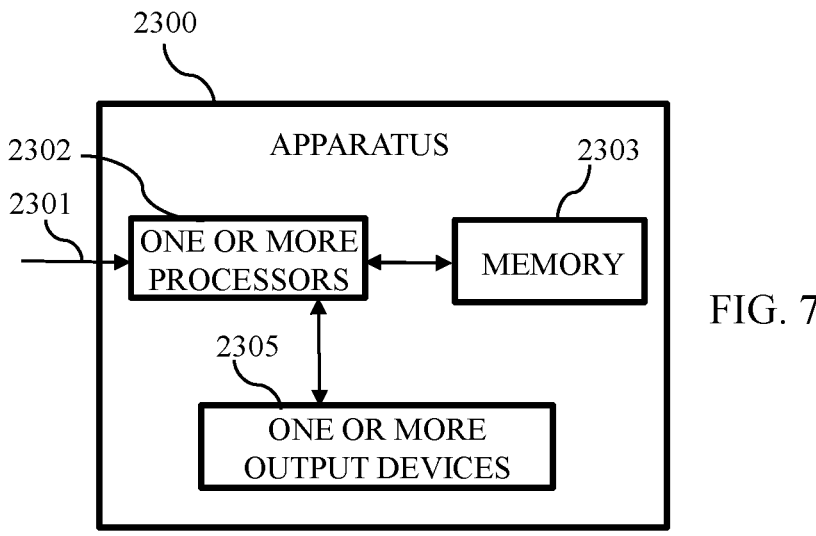
FIG. 7 depicts an example apparatus to detect an improper transducer configuration.

FIG. 7 depicts an exemplary apparatus 2300 to detect an improper transducer configuration. The apparatus 2300 may include one or more processors 2302, a memory 2303, one or more input devices, and one or more output devices 2305. The apparatus 2300 may be a computer. The apparatus 2300 may be incorporated into, or may be separate from and communicatively coupled to, the controller 2222 of FIG. 6. The memory 2303 is accessible by the one or more processors 2302, and the memory 2303 may store instructions that, when executed by the processor(s) 2302, cause the apparatus 2300 to perform one or more methods disclosed herein. Based on current/voltage measurement feedback or other information received as inputs 2301, the processor(s) 2302 may detect an improper configuration of one or more transducers on the subject's body and alert a user to the improper configuration via an output on the one or more output devices 2305. For example, the controller (e.g., 2222 of FIG. 6) may be configured to output an alert via the output device(s) 2305 upon detecting that a conductive wire has been cut, or upon detecting a short circuit between two adjacent transducers.

Figure 8A:
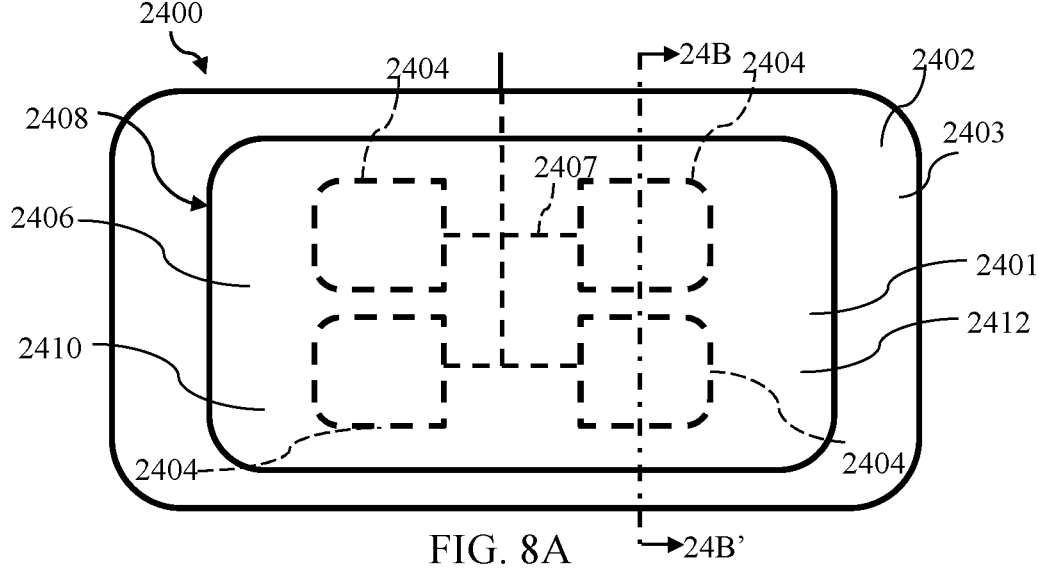
FIGS. 8A and 8B depict an example transducer with a conductive material layer.
Figure 8B:
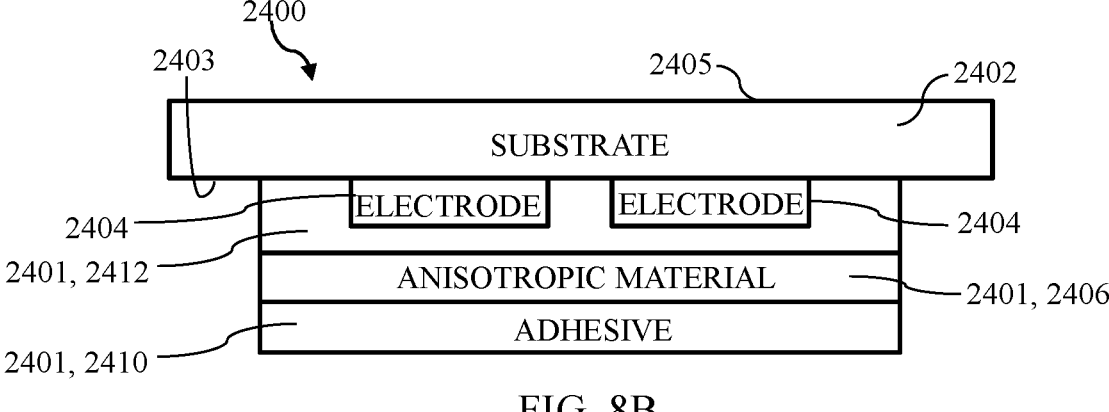
Figure 9A:
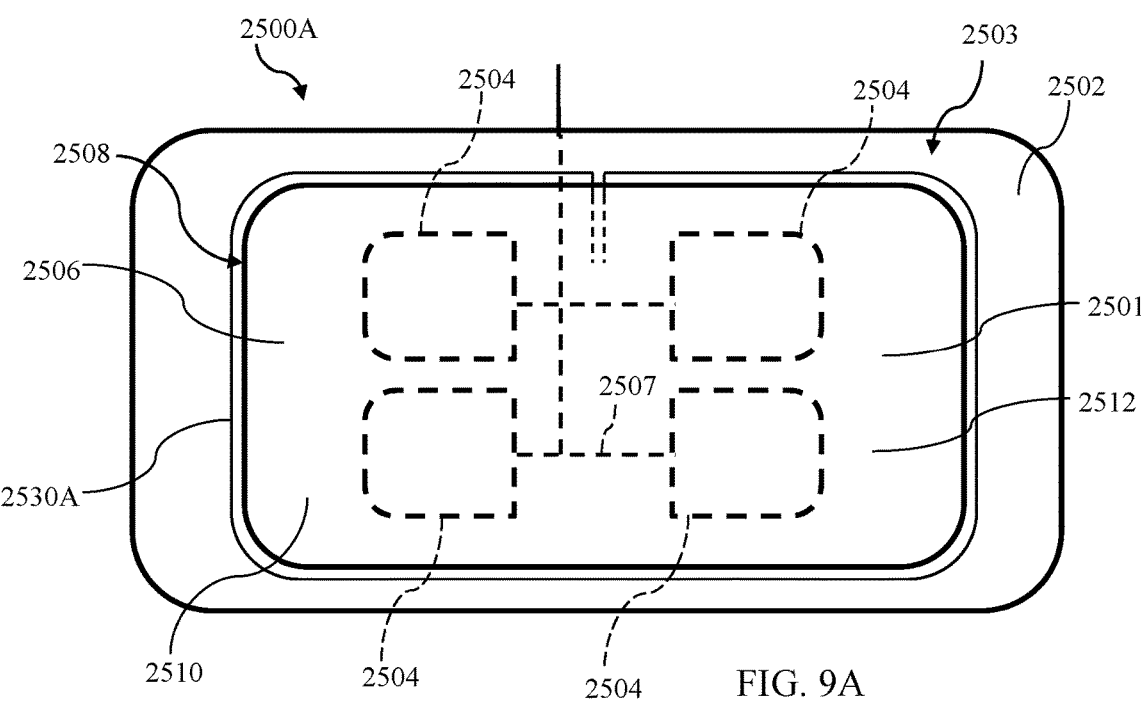
FIGS. 9A and 9B depict an example transducer with a conductive wire sensor.
Figure 9B:
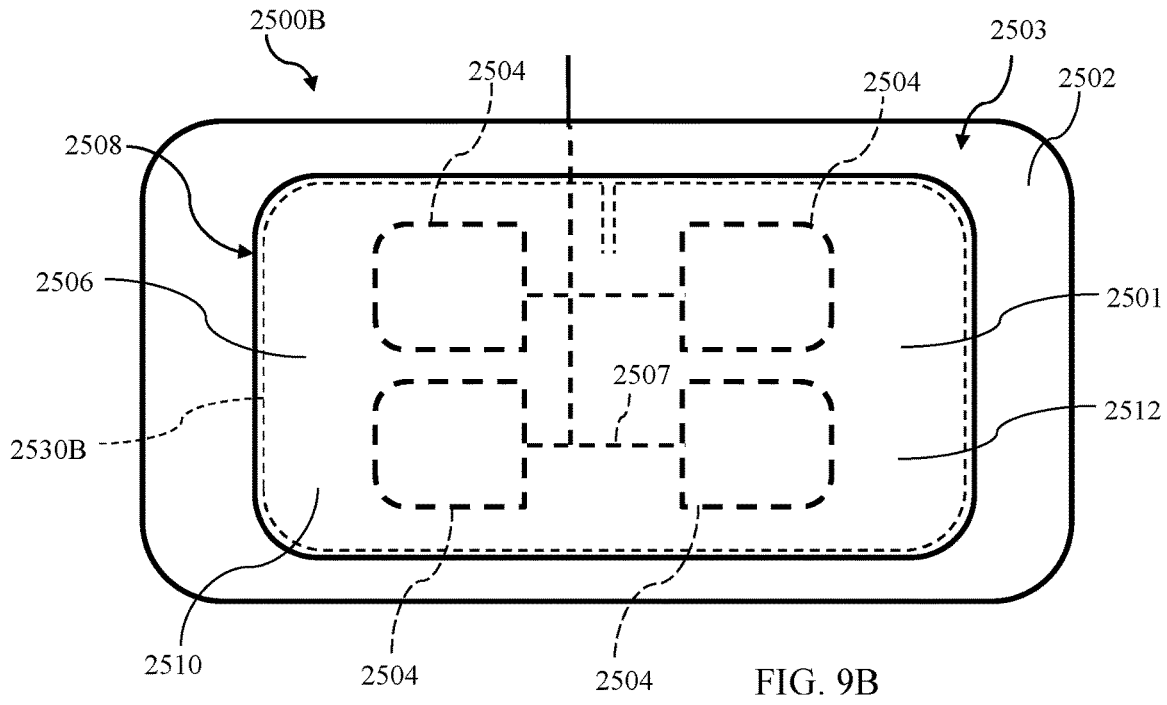

FIGS. 8A and 8B depict an example transducer 2400 with a layer of anisotropic material 2406. FIG. 8A is a bottom view (showing the skin facing front face) of the transducer 2400, and FIG. 8B is a side cross-sectional view of the transducer 2400 (taken at cross-section 24B-24B', FIG. 8A). FIGS. 9A and 9B depict example transducers 2500A-B with a conductive wire sensor 2930. FIGS. 9A and 9B are bottom views (showing the front face) of the transducers 2500A-B, respectively. Each transducer (2400, 2500A-B) of FIGS. 8A-9B is capable of delivering TTFields to a subject's body.

In FIGS. 8A-9B, each transducer (2400, 2500A-B) includes a substrate (2402, 2502) and at least one electrode element (2404, 2504) coupled to the substrate (2402, 2502) and a layer of anisotropic material (2406, 2506) coupled to the electrode element(s) (2404, 2504). The substrate (2402, 2502) has a front face (2403, 2503) and a back face (e.g., 2405), and the electrode element(s) (2404, 2504) are located on a side of the front face (2403, 2503) of the substrate (2402, 2502). As illustrated, the electrode element(s) (2404, 2504) are located between the substrate (2402, 2502) and the layer of anisotropic material (2406, 2506). As shown, the layer of anisotropic material (2406, 2506) may occupy an areal footprint (2408, 2508) in a plane parallel to the front face (2403, 2503) of the substrate (2402, 2502).

The transducer (2400, 2500A-B) of FIGS. 8A-9B may be affixed to the subject's body via the substrate (2402, 2502). In FIGS. 8A-9B, the transducers (2400, 2500A-B) comprise arrays of substantially flat electrode element(s) (2404, 2504). In each figure, the array of electrode elements (2404, 2504) may be capacitively coupled. In an example, the electrode elements (2404, 2504) are ceramic electrode elements coupled to each other via conductive wiring (2407, 2507). When viewed in a direction perpendicular to its face, the ceramic electrode elements may be circular shaped (e.g., 2204A-D in FIG. 6) or non-circular shaped (e.g., 2404 in FIG. 8A). In another example, the electrode elements (2404, 2504) may be non-ceramic dielectric materials positioned over a plurality of flat conductors (e.g., high dielectric constant polymer films disposed over pads on a printed circuit board or flex circuit or over substantially planar pieces of metal). When viewed in a direction perpendicular to its face, the non-ceramic electrode elements may take any desired shape.

The transducer (2400, 2500A-B) also includes at least one conductive material layer (2401, 2501). In some embodiments, the conductive material layer (2401, 2501) may be a layer of anisotropic material (2406, 2506) coupled to the at least one electrode element (2404, 2504). The electrode element(s) (2404, 2504) may be located between the substrate (2402, 2502) and the layer of anisotropic material (2406, 2506). In some embodiments, the conductive material layer (2401, 2501) may be a hydrogel layer or an electrically conductive adhesive layer electrically coupled to the at least one electrode element (2404, 2504). The hydrogel layer or electrically conductive adhesive layer may be located on an opposite side of the electrode element(s) (2404, 2504) from the substrate (2402, 2502). The hydrogel layer or electrically conductive adhesive layer may be a conductive skin contact adhesive layer (2410, 2510). The electrically conductive skin contact adhesive layer (2410, 2510) has a skin facing front face and a back face, with the back face facing the electrode element(s) (2404, 2504). As illustrated, when a layer of anisotropic material (2406, 2506) is present in the transducer (2400, 2500A-B), the layer of anisotropic material (2406, 2506) is located between the electrode element(s) (2404, 2504) and the skin contact adhesive layer (2410, 2510). Alternatively, or additionally, a hydrogel layer or electrically conductive adhesive layer may function as an upper adhesive layer (for example, 2412, 2512) located between the electrode element(s) (2404, 2504) and the layer of anisotropic material (2406, 2506). In some embodiments, the layer of anisotropic material (2406, 2506) is sandwiched between two layers of hydrogel, or sandwiched between two layers of electrically conductive adhesive, or sandwiched between one layer of each. As shown, the conductive material layer(s) (2401, 2501), which may include the layer of anisotropic material (2406, 2506), or one or more hydrogel layers or one or more electrically conductive adhesive layers, or a combination thereof, occupy an areal footprint (2408, 2508) in a plane parallel to the front face (2403, 2503) of the substrate (2402, 2502).

The layer of anisotropic material (2406, 2506) of FIGS. 8A-9B may be any conductive layer having different thermal and/or electrical conductivities in a direction perpendicular to the front face (2403, 2503) of the substrate (2402, 2502) than in directions that are parallel to the front face (2403, 2503). The layer of anisotropic material may be anisotropic with respect to electrical conductivity properties, anisotropic with respect to thermal properties, or both. This allows the layer of anisotropic material to spread out current and/or heat over a larger surface area. In each case, this lowers the temperature of hot spots and raises the temperature of cooler regions when a given AC voltage is applied to the array of electrode elements. Accordingly, the current can be increased without exceeding a safety temperature threshold at any point on the subject's skin. The layer of anisotropic material may be a sheet of pyrolytic graphite, graphitized polymer film, a foil made from compressed high purity exfoliated mineral graphite, or some other material. Details regarding such layers of anisotropic material and properties thereof are described in U.S. Patent Application Publication No. 2023/0037806 A1 (Wasserman et al., Feb. 9 2023), which is hereby incorporated by reference in the present disclosure.

The transducer (2400, 2500A-B) may further include one or more electrically conductive adhesive layers. For example, the transducer (2400, 2500) may include an electrically conductive adhesive layer (2410, 2510) located on a front face of the layer of anisotropic material and configured to contact the subject's skin. Additionally, or alternatively, as shown in FIG. 8B, the transducer 2400 may further include the electrically conductive upper adhesive layer 2412 located between the at least one electrode element 2404 and a back face of the layer of anisotropic material 2406. Electrically conductive adhesive layers may form part of the transducer's areal exclusion zone (2408, 2508). The upper adhesive layer 2412 may extend from the substrate 2402 to the layer of anisotropic material 2406. Alternatively, the upper adhesive layer 2412 may simply coat the front face of the at least one electrode element 2404 facing the layer of anisotropic material 2406. The transducers of FIGS. 9A and 9B may similarly include the electrically conductive upper adhesive layer 2512, which is located between electrode element(s) 2504 and a back face of the layer of anisotropic material 2506.

The electrically conductive skin contact adhesive layer (2410, 2510) and/or the electrically conductive upper adhesive layer (e.g., 2412, 2512) may be a composite adhesive layer. For example, the electrically conductive adhesive layer(s) (2410, 2510; or 2412, 2512) may comprise a plurality of electrically conductive particles embedded at least partially within an adhesive matrix material. The electrically conductive particles may provide enhanced electrical conductivity in the x-y plane of the adhesive layer. The electrically conductive particles may include carbon granules, carbon flakes, graphite powder, carbon black powder, carbon nanoparticles, carbon nanotubes, and the like. The electrically conductive particles may include electrically conductive fibers, such as carbon fibers, or carbon wires or nanowires. The electrically conductive particles may comprise graphite. The plurality of electrically conductive particles may comprise a sheet of fibers embedded in the adhesive matrix material. The sheet of fibers may be in the form of a mesh layer that can be cut to any desired shape, which becomes the areal footprint of the conductive material layer (2401, 2501). The electrically conductive fibers may be oriented such that the longitudinal axes of each of the fibers is substantially (e.g., within 20 degrees, or within 10 degrees) parallel to the x-y plane of the adhesive layer (2410, 2510; or 2412, 2512). In some embodiments, the electrically conductive fibers may provide enhanced electrical conductivity in the x-y plane of the adhesive layer. The adhesive matrix material may comprise any suitable polymer, for example, the adhesive matrix material may comprise an acrylic polymer matrix material or a silicone polymer matrix material. The conductive adhesive layer (2410, 2510; or 2412, 2512) may comprise a medical grade adhesive that requires no hydrogel or Ag/AgCl to get a signal, sold under the trademark FLEXcon® OMNI-WAVE™ (available from FLEXcon located in Spencer, Massachusetts).

In some embodiments, the electrically conductive adhesive layer (2410, 2510; or 2412, 2512) may not include a plurality of electrically conductive particles that provide enhanced electrical/heat conductivity in the x-y plane of the adhesive layer. In some embodiments, the layer of anisotropic material (2406, 2506) may be the only conductive material layer (2401, 2501). In other embodiments, the layer of anisotropic material may not be present in the transducer (2400, 2500A-B), such that one or more electrically conductive adhesive layers (2410, 2510; or 2412, 2512) are the only conductive material layer(s) (2401, 2501).

The one or more conductive material layer(s) (2401, 2501), which includes the layer of anisotropic material (2406, 2506), the electrically conductive skin contact adhesive layer (2410, 2510), or the electrically conductive upper adhesive layer (2412, 2512), or a combination thereof, may take any desired shape. For example, as shown in FIGS. 8A-9B, an outer perimeter of the conductive material layer (2401, 2501) may have a substantially square or rectangular shape, or substantially square or rectangular shape with rounded corners. As another example, the outer perimeter of the conductive material layer (2401, 2501) may have a circular, oval, ovoid, ovaloid, or elliptical shape. This outer perimeter may define the areal footprint (2408, 2508) of the conductive material layer(s).

Turning specifically to FIGS. 9A and 9B, the transducer 2500A-B may include a conductive wire 2530A-B, which forms a conductive wire sensor in the transducer. When viewed in a direction perpendicular to the front face 2503 of the substrate 2502, the substrate 2502 extends laterally outward beyond the areal footprint 2508 of the conductive material layer(s) 2501 (which may include the layer of anisotropic material 2506, the electrically conductive skin contact adhesive layer 2510, the electrically conductive upper adhesive layer 2512, or a combination thereof); and the wire 2530A-B substantially traces an area surrounding over 90% of the areal footprint 2508 of the conductive material layer 2501. As in FIG. 9A, the wire 2530A may substantially trace an area surrounding 100% of the areal footprint 2508 of the conductive material layer 2501. Wire 2530A-B may be adhered to the substrate. In FIG. 9B, the wire 2530B may be located within a perimeter of the layer of anisotropic material 2506, or conjoined to, the layer of anisotropic material 2506 along a perimeter of the layer of anisotropic material 2506.

The wire 2530A-B may be coupled to a voltage source applying a relatively low voltage (e.g., within a range of 100-200 Volts) to the wire 2530A-B. The voltage may be applied to the wire 2530A-B from an AC voltage generator (e.g., 2220 of FIG. 6) coupled to the transducer. In another example, the voltage may be applied to the wire 2530A-B from a voltage source on a printed circuit board (PCB) or flex circuit of the transducer 2500A-B. In an example, the wire 2530A-B may be a PCB line or flex circuit.

If the wire 2530A-B is cut by a user cutting the transducer 2500A-B, the wire 2530A-B will cease conducting current therethrough, indicating a break in the wire 2530A-B. A voltage, current, and/or impedance of the wire 2530A-B may be monitored to determine whether the wire is broken. Due to the placement of the wire 2530A-B relative to the areal footprint 2508 of the conductive material layer(s) 2501, a signal or indication that the wire 2530A-B is broken would indicate a potential issue with the conductive material layer(s) 2501. In an example, the conductive wire sensor is capable of detecting whether the transducer 2500A-B has been cut such that, when viewed in the direction perpendicular to the front face 2503 of the substrate 2502, the substrate 2502 no longer extends outward beyond the areal footprint 2508 of the conductive material layer(s) 2501 (which may include the layer of anisotropic material 2506, the electrically conductive adhesive layer(s), or both).

In this manner, the conductive wire sensor allows for the active detection of an exposure of the exclusion zone (e.g., layer of anisotropic material 2506, electrically conductive adhesive layer(s), or both) of the transducer 2500A-B and alerting an operator to this exposure. Alerting an operator to the exposure may prevent a short circuit from occurring due to an improperly cut transducer 2500A-B. Such an alert may be output, for example, in the form of a blinking light on the AC voltage generator (e.g., 2220 of FIG. 6).

Figure 10:
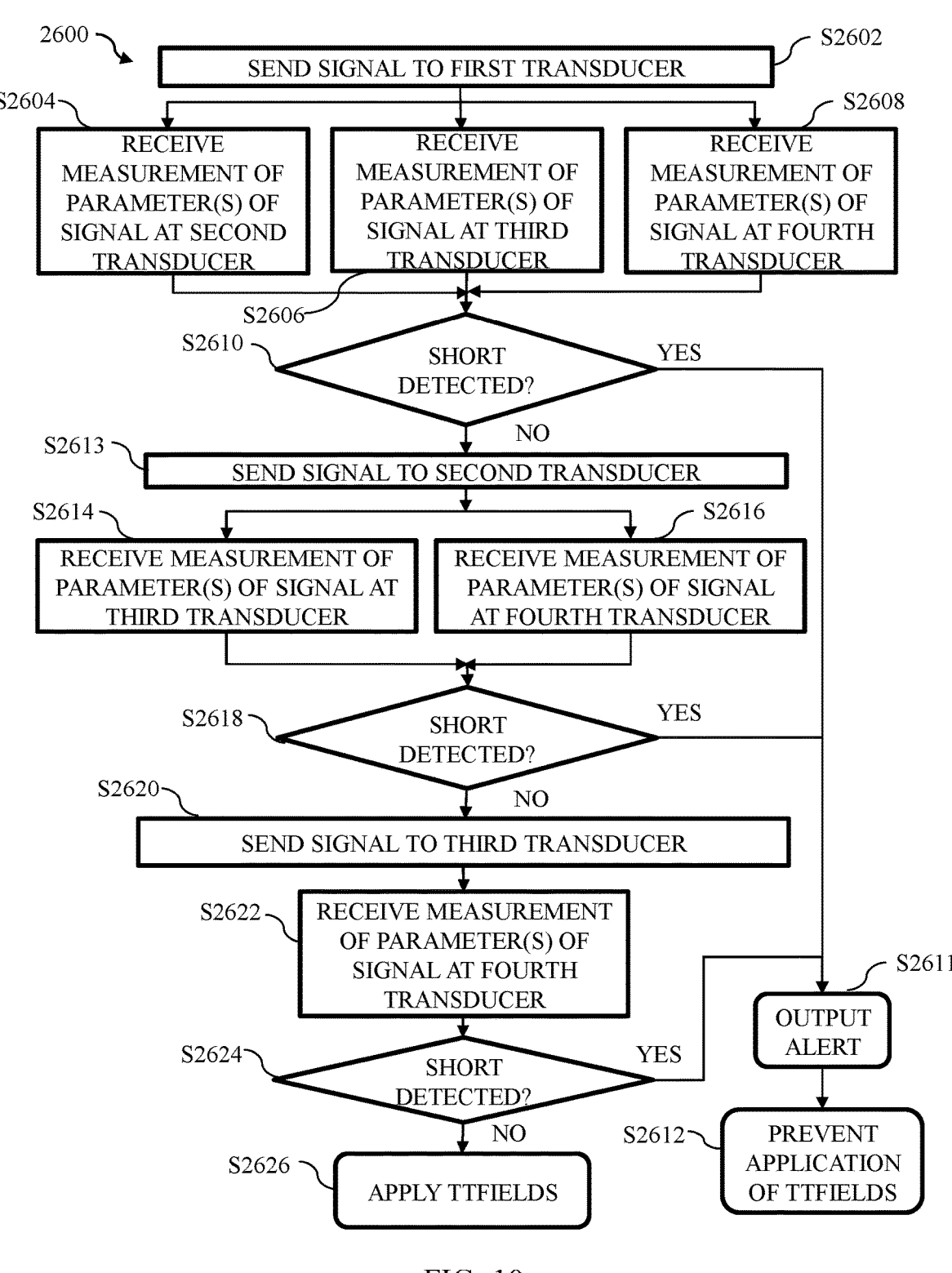
FIGS. 10-12 depict methods for detecting an improper configuration of transducers.
Figure 11:
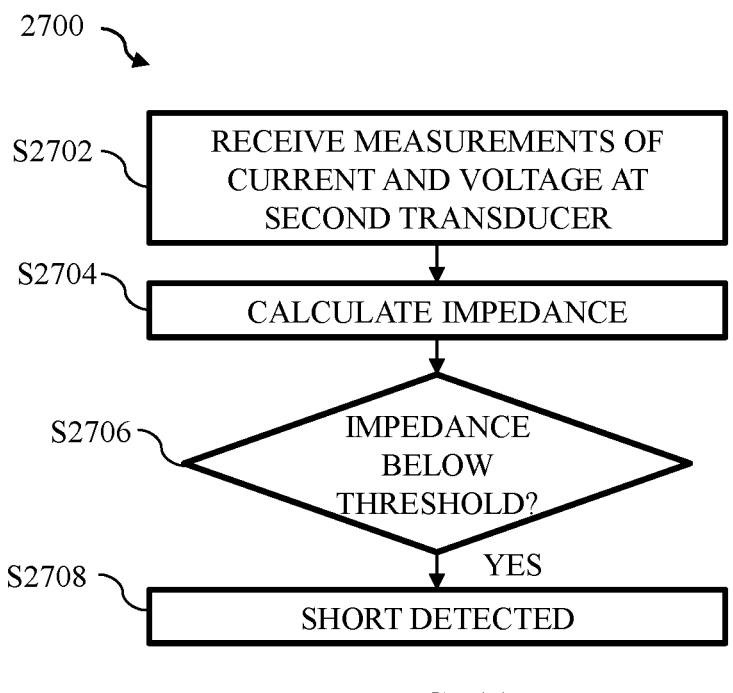
Figure 12:
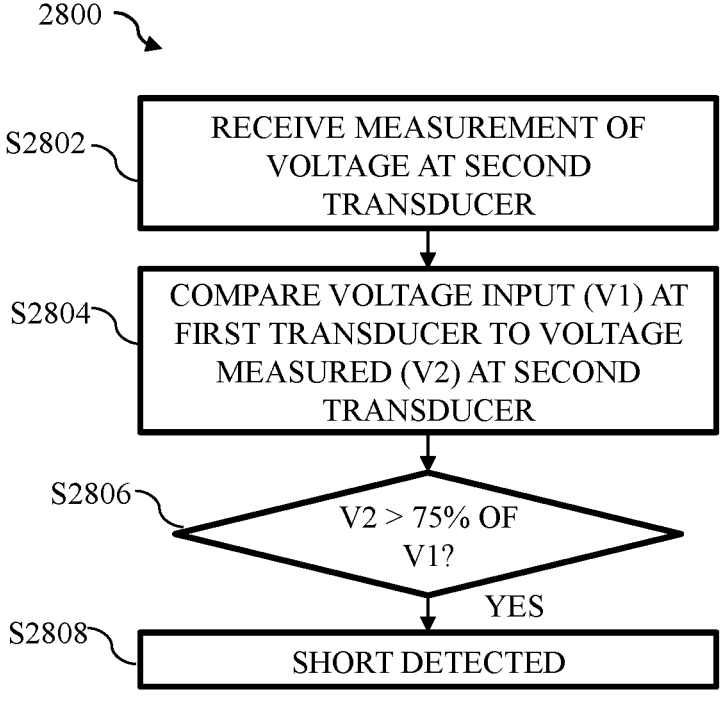

FIGS. 10-12 depict example methods (2600, 2700, 2800) for detecting an improper configuration of transducers on a subject's body. One or more steps may be computer-implemented steps. The computer may be any device having one or more processors and memory accessible by the processor(s), the memory storing instructions that when executed by the processor(s) cause the computer to perform relevant steps of the method. The computer may be the exemplary apparatus 2300. The methods (2600, 2700, 2800) may be used with transducers as disclosed with reference to any of FIGS. 8A-9B. The methods (2600, 2700, 2800) may be used with systems having at least a first transducer and a second transducer, the transducers being capable of applying TTFields to the subject's body. FIG. 10 illustrates a generalized method 2600 that may be used with systems having up to four transducers. FIGS. 11 and 12 illustrate specific example methods of different ways of detecting a short circuit, which may be applied in multiple steps of the generalized method 2600 of FIG. 10.

In FIG. 10 at step S2602, the method 2600 includes sending a first applied voltage signal (first signal) to a first transducer located on the subject's body. A frequency of the first applied voltage signal may be different than a frequency of a voltage signal capable of applying TTFields to the subject's body. The frequency of the first applied voltage signal may be between approximately 20 and 300 kHz. Step S2604 includes receiving measurements of one or more parameters of a first resulting signal (second signal) at a second transducer located on the subject's body. Step S2610 includes determining, based at least in part on the measurements of the one or more parameters, whether a short is present between the first and second transducers. Upon determining that a short is present, the method proceeds to step S2611, which includes outputting an alert via an output device. In response to determining that a short is present, the method 2600 may also include, at step S2612, preventing a voltage generator coupled to the transducers from sending a voltage signal capable of applying TTFields. In an example in which only two transducers are used, upon determining that no short is present, the method 2600 may proceed to step S2626, which includes applying, or outputting instructions to apply, a voltage capable of applying TTFields via the first and second transducers. That is, when only two transducers are used, intervening steps S2613, S2614, S2616, S2618, S2620, S2622 and S2624 (FIG. 10) are by-passed. One or more of steps S2604, S2610, S2611, S2612, and S2626 may be computer-implemented steps.

In a system having four transducers, the method 2600 may also include the following steps. At step S2606, the method 2600 may include receiving measurements of one or more parameters of a second resulting signal (third signal) received at a third transducer located on the subject's body in response to the first applied voltage signal applied at the first transducer. At step S2608, the method 2600 may include receiving measurements of one or more parameters of a third resulting signal (fourth signal) received at a fourth transducer located on the subject's body in response to the first applied voltage signal applied at the first transducer. Step S2610 may include determining, based at least in part on the measurements of the one or more parameters of the second resulting signal (third signal) and the third resulting signal (fourth signal), whether a short is present between the first and third transducers or between the first and fourth transducers. Upon determining that a short is present, the method 2600 proceeds to step(s) S2611 and/or S2612. One or more of steps S2606, S2608, and S2610 may be computer-implemented steps.

Upon determining that no short is present between the first transducer and any of the second, third, or fourth transducers, the method 2600 may proceed to step S2613. Step S2613 includes sending a second applied voltage signal (fifth signal) to the second transducer located on the subject's body. Step S2614 includes receiving measurements of one or more parameters of a fourth resulting signal (sixth signal) received at the third transducer in response to the second applied voltage signal applied to the second transducer. At step S2616, the method 2600 may include receiving measurements of one or more parameters of a fifth resulting signal (seventh signal) received at the fourth transducer in response to the second applied voltage signal applied at the second transducer. At step S2618, the method 2600 may include determining, based on the measurements of the one or more parameters of the fourth resulting signal and the fifth resulting signal, whether a short is present between the second and third transducers, or between the second and fourth transducers, respectively. If a short is present, the method 2600 proceeds to step(s) S2611 and/or S2612. Steps S2614, S2616, and S2618 may be computer-implemented steps.

If it is determined that no short is present at S2618, the method 2600 proceeds to step S2620: sending a third applied voltage signal (eighth signal) to the third transducer located on the subject's body. Step S2622 includes receiving measurements of one or more parameters of a sixth resulting signal (ninth signal) received at the fourth transducer in response to the third applied voltage signal applied to the third transducer. Step S2624 may include determining, based on the measurements of the parameters of the sixth resulting signal, whether a short is present between the third and fourth transducers. If it is determined that a short is present, the method 2600 proceeds to step(s) S2611 and/or S2612. Steps S2622 and S2624 may be computer-implemented steps.

Upon determining at S2610, S2618, and/or S2624 that no short is present, the method 2600 may proceed to step S2626: applying, or outputting instructions to apply, a voltage capable of applying TTFields via one or more single transducer or one or more pairs of transducers. For example, upon determining at step S2624 that no short is present, step S2626 may include applying, or outputting instructions to apply, voltage capable of applying TTFields via all four transducers.

FIG. 11 depicts an example method of detecting a short circuit between transducers on a subject's body based on impedance. Although method 2700 is illustrated as being applied to a single pair of transducers, it should be understood that it can be applied similarly for every pair of transducers in an arrangement of transducers on the subject's body. For example, step S2702 of the method 2700 may take the place of steps 2604, 2606, 2608, 2614, 2616, and/or 2622 in FIG. 10. Similarly, the combination of steps S2704 and S2706 may take the place of steps 2610, 2618, and/or 2624 for each pair of transducers in FIG. 10.

At step S2702, the method 2700 includes receiving measurements of a current and a voltage of a resulting voltage signal received at a second transducer in response to a voltage signal applied to the first transducer. At step S2704, the method 2700 includes calculating an impedance between the first transducer and the second transducer based on the measured current and voltage. At step S2706, the method 2700 includes comparing the impedance to a threshold impedance value. If the impedance is below the threshold impedance value, then a short is detected at step S2708. In an embodiment, the threshold impedance value may be less than the nominal impedance of the specific patient by three standard deviations. If the impedance between the two transducers is below the threshold impedance value, this would indicate that the transducers are touching and a short circuit is present.

Applying the steps of method 2700 to the method 2600 of FIG. 10 may include the following steps for a system having two transducers. The one or more parameters of measurements received at step S2604 include a voltage and a current. Step S2610 may include calculating an impedance between the first and second transducers via the measured voltage and current values; and comparing the impedance to a threshold impedance value.

Applying the steps of method 2700 to the method 2600 of FIG. 10 may include the following steps for a system having four transducers. The one or more parameters of measurements received at steps S2604, S2606, S2608, S2614, S2616, and S2622 include a voltage and a current. Steps S2610, S2618, and S2624 may together include calculating an impedance: 1) between the first and second transducers via the measured voltage and current values; 2) between the first and third transducers via the measured voltage and current values; 3) between the first and fourth transducers via the measured voltage and current values; 4) between the second and third transducers via the measured voltage and current values; 5) between the second and fourth transducers via the measured voltage and current value; 6) between the third and fourth transducers via the measured voltage and current values; and comparing each impedance to a threshold impedance value.

FIG. 12 depicts an example method of detecting a short circuit between transducers on a subject's body based on voltage only. Although method 2800 is illustrated as being applied to a single pair of transducers, it should be understood that it can be applied similarly for every pair of transducers in an arrangement of transducers on the subject's body. For example, step S2802 of the method 2800 may take the place of steps 2604, 2606, 2608, 2614, 2616, and/or 2622 in FIG. 10. Similarly, the combination of steps S2804 and S2806 may take the place of steps 2610, 2618, and/or 2624 for each pair of transducers in FIG. 10.

At step S2802, the method 2800 includes receiving a measurement of a second voltage at a second transducer resulting from a first voltage applied to the first transducer. At step S2804, the method 2800 includes comparing the second voltage to the first voltage. As an example, at step S2806, the method 2800 may include determining whether the second voltage is over 75% of the first voltage. However, other threshold percentages of the first voltage may be used in other embodiments to make the determination. For example, the step S2806 could instead be determining whether the second voltage is over 90% of the first voltage. At step S2808, the method 2800 includes detecting a short based on the comparison between the first voltage and the second voltage. If the voltage at the second transducer is similar to the voltage applied at the first transducer, this could indicate that the transducers are touching and a short circuit is present.

Applying the steps of method 2800 to the method 2600 of FIG. 10 may include the following steps for a system having two transducers. The one or more parameters of measurements received at step S2604 include a voltage. Step S2610 may include comparing an applied voltage applied to the first transducer to a resulting voltage measured at the second transducer. The applied voltage may be an amplitude of a voltage signal having a frequency between 20 and 300 kHz. The applied voltage may be between approximately 100 and 200 Volts.

Applying the steps of method 2800 to the method 2600 of FIG. 10 may include the following steps for a system having four transducers. The one or more parameters of measurements received at steps S2604, S2606, S2608, S2614, S2616, and S2622 include a voltage. Steps S2610, S2618, and S2624 may together include comparing a voltage applied to one of the first, second, third, and fourth transducers to a resulting voltage measured at another one of the first, second, third, and fourth transducers. For example, steps S2610, S2618, and S2624 may together include comparing: 1) an applied voltage applied to the first transducer to a resulting voltage measured at the second transducer; 2) an applied voltage applied to the first transducer to a resulting voltage measured at the third transducer; 3) an applied voltage applied to the first transducer to a resulting voltage measured at the fourth transducer; 4) an applied voltage applied to the second transducer to a resulting voltage measured at the third transducer; 5) an applied voltage applied to the second transducer to a resulting voltage measured at the fourth transducer; and 6) an applied voltage applied to the third transducer to a resulting voltage measured at the fourth transducer.

In an example, the methods (2600, 2700, 2800) disclosed herein may be performed prior to applying TTFields to a subject's body. In another example, the methods (2600, 2700, 2800) may be applied multiple times throughout a TTFields treatment period to account for any shifting in positions of transducers on the subject's body.

Figures 13A, 13B:
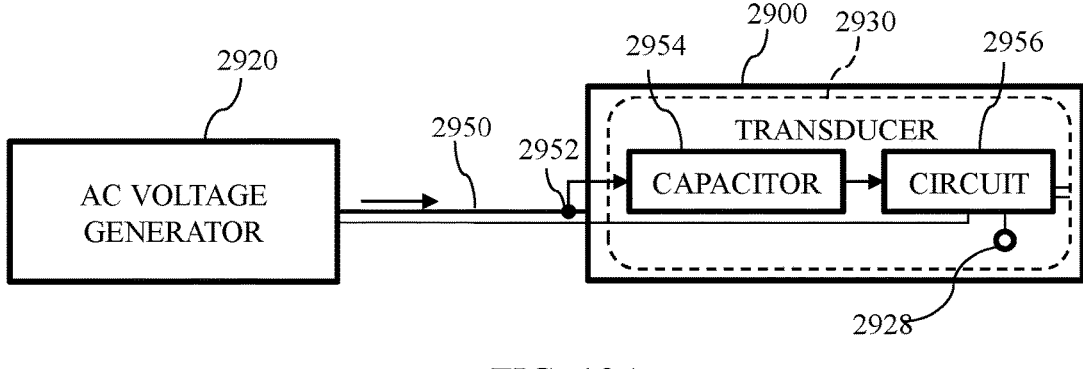
FIGS. 13A and 13B depict example systems for powering sensors on a transducer.

FIGS. 13A and 13B illustrate two example configurations for powering a conductive wire 2930 forming a conductive wire sensor on a transducer 2900. The wire 2930 may take the form of either of the wires 2530A-B described above with reference to FIGS. 9A and 9B. The voltage generator 2920 provides AC current to the transducer 2900, for example, via a conductor 2950 that permits AC current to flow between the voltage generator 2920 and the transducer 2900. In addition, a portion of the energy available from the voltage generator 2920 may be diverted to supply the low voltage to the wire 2930 and/or to operate one or more other sensors 2928 (e.g., temperature sensors) on the transducer

2900. As shown in FIG. 13A, the system may include a coil 2952 positioned to divert some of the energy that passes through the conductor 2950, and a capacitor 2954 arranged to store the diverted energy. The capacitor 2954 may be coupled to and supply power to adjacent circuitry 2956 used to control the sensors on the transducer 2900 and other related operations. For example, the energy may be diverted by the coil 2952 from a main conductor power source (e.g., the AC voltage generator 2920). Further, the energy may be stored locally in the capacitor 2954 for reuse in powering a circuit, wherein such circuit may be used, for example, for measuring temperature at thermistors and/or monitoring detection of a circuit break.

The circuitry 2956 powered by the diverted energy stored in the capacitor 2954 may include one or both of a wire-cut detection circuit and a temperature measurement circuit. In an example, the capacitor stored energy may be used by the circuitry 2956 (including a wire-cut detection circuit) to supply a voltage to the wire 2930, detect whether the wire 2930 has been cut, signal to the voltage generator 2920 (or associated controller) the status of the wire 2930, issue a warning signal, and/or power down the transducer 2900 in response to detecting the wire 2930 has been cut or detection of a short. In some embodiments, the circuitry 2956 may include a safety switch that may be used to halt power to the transducer 2900 in response to detection of either a cut wire or a detected short, and the switch may be activated using power stored in the capacitor 2954. The circuitry 2956 (including a temperature measurement circuit) may include a controller configured to obtain temperature readings from one or more temperature sensors 2928 on the transducer 2900, and generate digital data corresponding to the temperature readings. As such, the capacitor stored energy may be used by the circuitry 2956 to power the controller (or other similar means to generate digital data related to temperature measurement(s)) and/or send the digital data to the voltage generator 2920.

The circuitry 2956 and capacitor 2954 may be disposed in various locations. For example, as shown in FIG. 13A, the circuitry 2956 and capacitor 2954 may be integrated into the transducer 2900. As another example, shown in FIG. 13B, the circuitry 2956 and capacitor 2954 may be located in the AC voltage generator 2920. In this example, the coil (not shown) used to divert a portion of the AC voltage is also located in the voltage generator 2920. In other embodiments, the circuitry 2956 and capacitor 2954 may be located somewhere between the AC voltage generator 2920 and the transducer 2900. For example, the circuitry 2956 and/or capacitor 2954 may be located in a HUB or in a connector. In still other embodiments, more than one set of a coil 2952, capacitor 2954, and circuitry 2956 may be located within the system at a combination of the above-described locations.

The invention includes other illustrative embodiments ("Embodiments") as follows.

Embodiment 1: A transducer apparatus for delivering tumor treating fields to a subject's body, the transducer apparatus comprising: a substrate; at least one electrode element coupled to the substrate; a layer of anisotropic material electrically coupled to the at least one electrode element, wherein the at least one electrode element is located between the substrate and the layer of anisotropic material, the layer of anisotropic material having a front face and a back face, wherein the back face of the layer of anisotropic material faces the at least one electrode element; a non-conductive material border disposed over at least a portion of an outer perimeter of the layer of anisotropic material, the non-conductive material border being electrically non-conductive, wherein, when viewed in a direction perpendicular to the front face of the layer of anisotropic material: an inner edge of the non-conductive material border overlaps a portion of the front face of the layer of anisotropic material, and an outer edge of the non-conductive material border extends outside the outer perimeter of the layer of anisotropic material.

Embodiment 2: The transducer apparatus of Embodiment 1, wherein, when viewed in the direction perpendicular to the front face of the layer of anisotropic material: the inner edge of the non-conductive material border overlaps the front face of the layer of anisotropic material along an entire length of the inner edge, and the outer edge of the non-conductive material border extends outside the outer perimeter of the layer of anisotropic material along an entire length of the non-conductive material border such that all of the outer perimeter of the layer of anisotropic material is covered by the non-conductive material border. Embodiment 3: The transducer apparatus of Embodiment 1, wherein, when viewed in a direction parallel to the front face of the layer of anisotropic material: the non-conductive material border covers a full thickness of the layer of anisotropic material in the direction perpendicular to the front face of the layer of anisotropic material. Embodiment 4: The transducer apparatus of Embodiment 1, wherein the non-conductive material border is adhered to a front face of the substrate, the front face of the substrate facing the at least one electrode element. Embodiment 5: The transducer apparatus of Embodiment 1, wherein, when viewed in the direction perpendicular to the front face of the layer of anisotropic material: the outer edge of the non-conductive material border extends at least 1 mm outside of the outer perimeter of the layer of anisotropic material. Embodiment 6: The transducer apparatus of Embodiment 1, wherein the non-conductive material border comprises a non-conductive adhesive. Embodiment 7: The transducer apparatus of Embodiment 1, wherein the non-conductive material border comprises a tape, bandage or plaster. Embodiment 8: The transducer apparatus of Embodiment 1, wherein the non-conductive material border comprises a tape, bandage or plaster, wherein the tape, bandage or plaster adheres to the front face, or on a front facing side, of the layer of anisotropic material within the outer perimeter of the layer of anisotropic material and is folded to adhere to the back face, or on a back facing side, of the layer of anisotropic material. Embodiment 9: The transducer apparatus of Embodiment 1, wherein the layer of anisotropic material has different thermal and/or electrical conductivities in a direction perpendicular to the front face than in directions that are parallel to the front face. Embodiment 10: The transducer apparatus of Embodiment 1, further comprising at least one of: an electrically conductive adhesive layer located on the front face of the layer of anisotropic material between the layer of anisotropic material and the non-conductive material border, or an electrically conductive adhesive layer located between the at least one electrode element and the back face of the layer of anisotropic material. Embodiment 11: The transducer apparatus of Embodiment 1, wherein the outer perimeter of the layer of anisotropic material has a circular, oval, ovoid, ovaloid, or elliptical shape, or substantially square or rectangular shape, or substantially square or rectangular shape with rounded corners. Embodiment 12: The transducer apparatus of Embodiment 1, wherein the at least one electrode element comprises a ceramic electrode element. Embodiment 13: The transducer apparatus of Embodiment 1, wherein the at least one electrode element comprises a polymer film.

Embodiment 14: A transducer apparatus for delivering tumor treating fields to a subject's body, the transducer apparatus comprising: a substrate having a front face and a back face; at least one electrode element coupled to the substrate and located on a side of the front face of the substrate; a layer of anisotropic material electrically coupled to the at least one electrode element, wherein the at least one electrode element is located between the substrate and the layer of anisotropic material; and a visual indicator that is visible from a side of the back face of the substrate; wherein, when viewed from a direction perpendicular to the back face of the substrate: the visual indicator indicates a border surrounding an areal exclusion zone of the transducer apparatus, the areal exclusion zone containing at least an areal footprint of the layer of anisotropic material.

Embodiment 15: The transducer apparatus of Embodiment 14, wherein the visual indicator comprises at least one solid, dashed, ticked, or otherwise patterned line on the back face of the substrate, or visible from the back side of the substrate, tracing the border surrounding the areal exclusion zone. Embodiment 16: The transducer apparatus of Embodiment 15, wherein the visual indicator further comprises text on the substrate. Embodiment 17: The transducer apparatus of Embodiment 16, wherein the text identifies a region in which to cut the substrate, a region where not to cut the substrate, or both. Embodiment 18: The transducer apparatus of Embodiment 14, wherein the visual indicator comprises an area of the substrate located inside the border surrounding the areal exclusion zone having a different color or pattern than an area of the substrate located outside the border surrounding the areal exclusion zone. Embodiment 19: The transducer apparatus of Embodiment 14, wherein the visual indicator comprises a visually identifiable raised portion of the surface of the substrate along the border surrounding the areal exclusion zone due to the presence of an additional material layer coupled to the substrate. Embodiment 20: The transducer apparatus of Embodiment 19, wherein the additional material layer increases a thickness of the substrate in the direction perpendicular to the back face of the substrate. Embodiment 21: The transducer apparatus of Embodiment 14, wherein, when viewed from the direction perpendicular to the back face of the substrate: the border surrounding the areal exclusion zone extends at least 1 mm outside of the areal footprint of the layer of anisotropic material on all sides. Embodiment 22: The transducer apparatus of Embodiment 14, wherein the border has a circular, oval, ovoid, ovaloid, or elliptical shape, or substantially square or rectangular shape, or substantially square or rectangular shape with rounded corners.

Embodiment 23: A transducer apparatus for delivering tumor treating fields to a subject's body, the transducer apparatus comprising: a substrate having a front face and a back face; at least one electrode element coupled to the substrate and located on a side of the front face of the substrate; a layer of anisotropic material electrically coupled to the at least one electrode element, wherein the at least one electrode element is located between the substrate and the layer of anisotropic material; and a cut-resistant material layer coupled to the substrate; wherein, when viewed from a direction perpendicular to the front face of the substrate: the cut-resistant material layer defines a border surrounding an areal exclusion zone of the transducer apparatus, the areal exclusion zone containing at least an areal footprint of the layer of anisotropic material. Embodiment 24: The transducer apparatus of Embodiment 23, wherein the cut-resistant material layer is configured to prevent, deter, or reduce the amount by which a user can cut through the combined substrate and cut-resistant material layer with scissors. Embodiment 25: The transducer apparatus of Embodiment 23, wherein the cut-resistant material layer is made from a thermosetting or thermoplastic polymeric material, a reinforced polymeric material, a reinforced fabric, or a combination thereof. Embodiment 26: The transducer apparatus of Embodiment 23, wherein a combined thickness of the substrate and the cut-resistant material layer is greater than 500 μm in the direction perpendicular to the front face of the substrate. Embodiment 27: The transducer apparatus of Embodiment 23, wherein the at least one electrode element is located on a side of the front face of the substrate, and wherein the cut-resistant material layer is coupled to the front face of the substrate. Embodiment 28: The transducer apparatus of Embodiment 27, further comprising a visual indicator on the back face of the substrate, the visual indicator indicating the location of the border defined by the cut-resistant material layer. Embodiment 29: The transducer apparatus of Embodiment 23, wherein the at least one electrode element is located on a side of the front face of the substrate, and wherein the cut-resistant material layer is coupled to the back face of the substrate. Embodiment 30: The transducer apparatus of Embodiment 23, wherein the cut-resistant material layer is coupled to the substrate via adhesive. Embodiment 31: The transducer apparatus of Embodiment 23, wherein, when viewed from the direction perpendicular to the front face of the substrate: the border surrounding the areal exclusion zone extends at least 1 mm outside of the areal footprint of the layer of anisotropic material on all sides. Embodiment 32: The transducer apparatus of Embodiment 23, wherein, when viewed from the direction perpendicular to the front face of the substrate: the cut-resistant material layer does not overlap the entirety of the areal exclusion zone, the cut-resistant material layer comprising: an outer edge that defines the border surrounding the areal exclusion zone; and an inner edge that defines an opening within the cut-resistant material layer. Embodiment 33: The transducer apparatus of Embodiment 23, wherein, when viewed from the direction perpendicular to the front face of the substrate: the cut resistant material layer overlaps the entirety of the areal exclusion zone.

Embodiment 34: A transducer apparatus for delivering tumor treating fields to a subject's body, the transducer apparatus comprising: a substrate having a front face and a back face; at least one electrode element coupled to the substrate; a layer of anisotropic material electrically coupled to the at least one electrode element, wherein the at least one electrode element is located between the substrate and the layer of anisotropic material; and a border defined by a physical barrier, a visual indication on the substrate, or both; wherein, when viewed in a direction perpendicular to the front face of the substrate: the border surrounds an areal exclusion zone of the transducer apparatus, the areal exclusion zone containing at least an areal footprint of the layer of anisotropic material.

Embodiment 35: A transducer apparatus for delivering tumor treating fields to a subject's body, the transducer apparatus comprising: a substrate; at least one electrode element coupled to the substrate; a layer of anisotropic material electrically coupled to the at least one electrode element, wherein the at least one electrode element is located between the substrate and the layer of anisotropic material, the layer of anisotropic material having a front face and a back face, wherein the back face of the layer of anisotropic material faces the at least one electrode element; a non-conductive adhesive applied outside of an outer perimeter of the layer of anisotropic material, the non-conductive adhesive being electrically non-conductive, wherein, when viewed in a direction perpendicular to the front face of the layer of anisotropic material: an inner edge of the non-conductive adhesive starts at the outer perimeter of the layer of anisotropic material, and an outer edge of the non-conductive adhesive extends outside the outer perimeter of the layer of anisotropic material; or an inner edge of the non-conductive adhesive starts outside the outer perimeter of the layer of anisotropic material, and an outer edge of the non-conductive adhesive extends further outside the outer perimeter of the layer of anisotropic material.

Embodiment 36: The transducer apparatus of any one of the previous embodiments, wherein the layer of anisotropic material comprises graphite. Embodiment 37: The transducer apparatus of any one of the previous embodiments, wherein the layer of anisotropic material comprises pyrolytic graphite, graphitized polymer, or graphite foil made from compressed high purity exfoliated mineral graphite.

Embodiment 37: A transducer apparatus for delivering tumor treating fields to a subject's body, the transducer apparatus comprising: a substrate; at least one electrode element coupled to the substrate; an electrically conductive adhesive layer located on an opposite side of the at least one electrode element from the substrate, the electrically conductive adhesive layer having a front face and a back face, wherein the back face of the electrically conductive adhesive layer faces the at least one electrode element; a non-conductive material border disposed over an outer perimeter of the electrically conductive adhesive layer, the non-conductive material border being electrically non-conductive, wherein, when viewed in a direction perpendicular to the front face of the electrically conductive adhesive layer: an inner edge of the non-conductive material border overlaps a portion of the front face of the electrically conductive adhesive layer, and an outer edge of the non-conductive material border extends outside the outer perimeter of the electrically conductive adhesive layer.

Embodiment 38: The transducer apparatus of Embodiment 37, wherein, when viewed in the direction perpendicular to the front face of the electrically conductive adhesive layer: the inner edge of the non-conductive material border overlaps the front face of the electrically conductive adhesive layer along an entire length of the inner edge, and the outer edge of the non-conductive material border extends outside the outer perimeter of the electrically conductive adhesive layer along an entire length of the non-conductive material border such that all of the outer perimeter of the electrically conductive adhesive layer is covered by the non-conductive material border. Embodiment 39: The transducer apparatus of Embodiment 37, wherein, when viewed in a direction parallel to the front face of the electrically conductive adhesive layer: the non-conductive material border covers a full thickness of the electrically conductive adhesive layer in the direction perpendicular to the front face of the electrically conductive adhesive layer. Embodiment 40: The transducer apparatus of Embodiment 37, wherein the electrically conductive adhesive layer comprises an adhesive matrix material; and a plurality of electrically conductive particles embedded at least partially within the adhesive matrix material. Embodiment 41: The transducer apparatus of Embodiment 40, wherein the plurality of electrically conductive particles are fibers. Embodiment 42: The transducer apparatus of Embodiment 40, wherein the plurality of electrically conductive particles comprise graphite. Embodiment 43: The transducer apparatus of Embodiment 40, wherein the plurality of electrically conductive particles comprises a sheet of fibers embedded in the adhesive matrix material. Embodiment 44: The transducer apparatus of Embodiment 37, further comprising a layer of anisotropic material located between one or more than one electrode element and the electrically conductive adhesive layer. Embodiment 45: The transducer apparatus of Embodiment 44, further comprising a second electrically conductive adhesive layer located between the one or more than one electrode element and the layer of anisotropic material. Embodiment 46: The transducer apparatus of Embodiment 45, wherein at least one electrically conductive adhesive layer comprises carbon fibers.

Embodiment 47: A transducer apparatus for delivering tumor treating fields to a subject's body, the transducer apparatus comprising: a substrate; at least one electrode element coupled to the substrate; a conductive material layer electrically coupled to the at least one electrode element, wherein the at least one electrode element is located between the substrate and the conductive material layer, the conductive material layer having a front face and a back face, wherein the back face of the conductive material layer faces the at least one electrode element; a non-conductive material border disposed over an outer perimeter of the conductive material layer, the non-conductive material border being electrically non-conductive, wherein, when viewed in a direction perpendicular to the front face of the conductive material layer: an inner edge of the non-conductive material border overlaps a portion of the front face of the conductive material layer, and an outer edge of the non-conductive material border extends outside the outer perimeter of the conductive material layer.

Embodiment 48: A transducer apparatus for delivering tumor treating fields to a subject's body, the transducer apparatus comprising: a substrate having a front face and a back face; at least one electrode element coupled to the substrate and located on a side of the front face of the substrate; a conductive material layer electrically coupled to the at least one electrode element, wherein the at least one electrode element is located between the substrate and the conductive material layer; and a visual indicator that is visible from a side of the back face of the substrate; wherein, when viewed from a direction perpendicular to the back face of the substrate: the visual indicator indicates a border surrounding an areal exclusion zone of the transducer apparatus, the areal exclusion zone containing at least an areal footprint of the conductive material layer.

Embodiment 49: A transducer apparatus for delivering tumor treating fields to a subject's body, the transducer apparatus comprising: a substrate having a front face and a back face; at least one electrode element coupled to the substrate and located on a side of the front face of the substrate; a conductive material layer electrically coupled to the at least one electrode element, wherein the at least one electrode element is located between the substrate and the conductive material layer; and a cut-resistant material layer coupled to the substrate; wherein, when viewed from a direction perpendicular to the front face of the substrate: the cut-resistant material layer defines a border surrounding an areal exclusion zone of the transducer apparatus, the areal exclusion zone containing at least an areal footprint of the conductive material layer.

Embodiment 50: The transducer apparatus of any of Embodiments 47, 48, or 49, wherein the conductive material layer comprises a layer of anisotropic material or an electrically conductive adhesive layer.

Embodiment 51: A system for delivering tumor treating fields to a subject's body, the system comprising: a transducer comprising: a substrate having a front face and a back face; at least one electrode element coupled to the substrate on a side of the front face of the substrate; a layer of anisotropic material electrically coupled to the at least one electrode element, wherein the layer of anisotropic material occupies an areal footprint in a plane parallel to the front face of the substrate; and a conductive wire, the wire forming a sensor in the transducer; wherein, when viewed in a direction perpendicular to the front face of the substrate: the substrate extends laterally outward beyond the areal footprint of the layer of anisotropic material; and the wire substantially traces an area surrounding over 90% of the areal footprint of the layer of anisotropic material.

Embodiment 52: The system of Embodiment 51, wherein, when viewed in the direction perpendicular to the front face of the substrate: the wire substantially traces an area surrounding 100% of the areal footprint of the layer of anisotropic material. Embodiment 53: The system of Embodiment 51, wherein the wire is adhered to the substrate. Embodiment 54: The system of Embodiment 51, wherein the wire is located within, or conjoined to, the layer of anisotropic material along a perimeter of the layer of anisotropic material. Embodiment 55: The system of Embodiment 51, wherein the wire is a printed circuit board (PCB) line or flex circuit line. Embodiment 56: The system of Embodiment 51, further comprising: a voltage generator coupled to the transducer and capable of inducing tumor treating fields between the transducer and another transducer; and a controller communicatively coupled to the voltage generator and capable of controlling the output of the voltage generator. Embodiment 57: The system of Embodiment 56, wherein the voltage generator or the controller supplies a voltage to the wire. Embodiment 58: The system of Embodiment 56, further comprising an output device communicatively coupled to the controller, wherein the controller is configured to output an alert via the output device upon detecting that the wire has been cut. Embodiment 59: The system of Embodiment 51, wherein the sensor is capable of detecting whether the transducer has been cut such that, when viewed in the direction perpendicular to the front face of the substrate, the substrate no longer extends outward beyond the areal footprint of the layer of anisotropic material. Embodiment 60: The system of Embodiment 51, further comprising: a voltage generator coupled to the transducer and capable of inducing tumor treating fields between the transducer and another transducer; a coil positioned to divert some of the energy supplied by the voltage generator; a capacitor arranged to store the diverted energy; and a circuit coupled to the wire to supply a voltage to the wire and detect whether the wire is cut, wherein the circuit is powered by the energy that is stored in the capacitor.

Embodiment 61: A method for detecting an improper configuration of transducers on a subject's body, the transducers comprising at least a first transducer and a second transducer, and the transducers being capable of applying tumor treating fields to the subject's body, the method comprising: sending a first applied voltage signal to the first transducer located on the subject's body; receiving measurements of one or more parameters of a first resulting signal at the second transducer located on the subject's body; determining, based at least in part on the measurements of the one or more parameters, whether a short is present between the first and second transducers; and upon determining that a short is present, outputting an alert via an output device.

Embodiment 62: The method of Embodiment 61, further comprising, in response to determining that a short is present, preventing a voltage generator coupled to the transducers from sending a voltage signal capable of applying tumor treating fields. Embodiment 63: The method of Embodiment 61, further comprising: upon determining that no short is present, applying a voltage capable of applying tumor treating fields via the first and second transducers. Embodiment 64: The method of Embodiment 61, wherein: the one or more parameters comprise a voltage and a current; and determining whether a short is present comprises: calculating an impedance between the first and second transducers via the measured voltage and current values; and comparing the impedance to a threshold impedance value. Embodiment 65: The method of Embodiment 61, wherein: the one or more parameters comprise a voltage; and determining whether a short is present comprises: comparing an applied voltage applied to the first transducer to a resulting voltage measured at the second transducer. Embodiment 66: The method of Embodiment 61, the transducers further comprising a third transducer and a fourth transducer, the method further comprising: receiving measurements of one or more parameters of a second resulting signal received at the third transducer in response to the first applied voltage signal applied at the first transducer; receiving measurements of one or more parameters of a third resulting signal received at the fourth transducer in response to the first applied voltage signal applied at the first transducer; determining, based at least in part on the measurements of the one or more parameters of the second resulting signal and the third resulting signal, whether a short is present between the first and third transducers or between the first and fourth transducers; and upon determining that a short is present, outputting an alert via the output device. Embodiment 67: The method of Embodiment 66, further comprising: receiving measurements of one or more parameters of a fourth resulting signal received at the third transducer in response to a second applied voltage signal applied to the second transducer; receiving measurements of one or more parameters of a fifth resulting signal received at the fourth transducer in response to the second applied voltage signal applied at the second transducer; receiving measurements of one or more parameters of a sixth resulting signal received at the fourth transducer in response to a third applied voltage signal applied to the third transducer; determining, based at least in part on the measurements of the one or more parameters of the fourth resulting signal, the fifth resulting signal, and sixth resulting signal, whether a short is present between the second and third transducers, or between the second and fourth transducers, or between the third and fourth transducers, respectively; and upon determining that a short is present, outputting an alert via the output device. Embodiment 68: The method of Embodiment 67, further comprising, in response to determining that a short is present, preventing a voltage generator coupled to the transducers from sending a voltage signal capable of applying tumor treating fields. Embodiment 69: The method of Embodiment 67, further comprising: upon determining that no short is present, applying a voltage capable of applying tumor treating fields via any one or more single transducer or via any one or more pairs of transducers. Embodiment 70: The method of Embodiment 67, wherein: the one or more parameters comprise a voltage and a current; and determining whether a short is present comprises: calculating an impedance: between the first and second transducers via the measured voltage and current values; between the first and third transducers via the measured voltage and current values; between the first and fourth transducers via the measured voltage and current values; between the second and third transducers via the measured voltage and current values; between the second and fourth transducers via the measured voltage and current value; between the third and fourth transducers via the measured voltage and current values; and comparing each impedance to a threshold impedance value. Embodiment 71: The method of Embodiment 67, wherein: the one or more parameters comprise a voltage; and determining whether a short is present comprises: comparing: an applied voltage applied to the first transducer to a resulting voltage measured at the second transducer; an applied voltage applied to the first transducer to a resulting voltage measured at the third transducer; an applied voltage applied to the first transducer to a resulting voltage measured at the fourth transducer; an applied voltage applied to the second transducer to a resulting voltage measured at the third transducer; an applied voltage applied to the second transducer to a resulting voltage measured at the fourth transducer; an applied voltage applied to the third transducer to a resulting voltage measured at the fourth transducer. Embodiment 72: The method of Embodiment 61, wherein the first and second transducers each comprise a substrate, an electrode element, and a layer of anisotropic material. Embodiment 73: The method of Embodiment 61, wherein the first and second transducers each comprise a substrate, an electrode element, and an electrically conductive adhesive material layer.

Embodiment 74: A computer-implemented method for detecting an improper configuration of transducers on a subject's body, the transducers comprising at least a first transducer and a second transducer, and the transducers being capable of applying tumor treating fields to a subject's body, the computer comprising one or more processors and memory accessible by the one or more processors, the memory storing instructions that when executed by the one or more processors cause the computer to perform the method, the method comprising: receiving measurements of a first current and a first voltage of a first resulting voltage signal received at the second transducer in response to a first voltage signal applied to the first transducer; calculating a first impedance between the first transducer and the second transducer based on the first current and the first voltage; comparing the first impedance to a threshold impedance value; and upon determining the first impedance is below the threshold impedance value, outputting an alert via an output device.

Embodiment 75: The computer-implemented method of Embodiment 74, wherein the threshold impedance value is less than the nominal impedance of the specific patient by three standard deviations. Embodiment 76: The computer-implemented method of Embodiment 74, wherein a frequency of the first voltage signal is between 20 and 300 kHz. Embodiment 77: The computer-implemented method of Embodiment 74, wherein a frequency of the first voltage signal is different than a frequency of a voltage signal capable of applying tumor treating fields to the subject's body. Embodiment 78: The computer-implemented method of Embodiment 74, further comprising, in response to determining the first impedance is below the threshold impedance value, outputting instructions to prevent a voltage generator coupled to the transducers from sending a voltage signal capable of applying tumor treating fields. Embodiment 79: The computer-implemented method of Embodiment 74, further comprising: receiving measurements of a second current and a second voltage of a second resulting voltage signal received at a third transducer in response to the first voltage signal at the first transducer; receiving measurements of a third current and a third voltage of a third resulting voltage signal received at a fourth transducer in response to the first voltage signal at the first transducer; calculating a second impedance between the first transducer and the third transducer based on the second current and the second voltage; calculating a third impedance between the first transducer and the fourth transducer based on the third current and the third voltage; comparing each of the second and third impedances to the threshold impedance value; and upon determining that either of the second impedance or the third impedance is below the threshold impedance value, outputting an alert via the output device. Embodiment 80: The computer-implemented method of Embodiment 79, further comprising: receiving measurements of a fourth current and a fourth voltage of a fourth resulting voltage signal received at the third transducer in response to a second voltage signal applied to the second transducer; receiving measurements of a fifth current and a fifth voltage of a fifth resulting voltage signal received at the fourth transducer in response to the second voltage signal at the second transducer; calculating a fourth impedance between the second transducer and the third transducer based on the fourth current and the fourth voltage; calculating a fifth impedance between the second transducer and the fourth transducer based on the fifth current and the fifth voltage; receiving measurements of a sixth current and a sixth voltage of a sixth resulting voltage signal received at the fourth transducer in response to a third voltage signal applied to the third transducer; calculating a sixth impedance between the third transducer and the fourth transducer based on the sixth current and the sixth voltage; comparing each of the fourth, fifth, and sixth impedances to the threshold impedance value; and upon determining that one or more of the fourth impedance, the fifth impedance, or the sixth impedance is below the threshold impedance value, outputting an alert via the output device. Embodiment 81: The computer-implemented method of Embodiment 80, further comprising, upon determining that each of the first impedance, the second impedance, the third impedance, the fourth impedance, the fifth impedance, and the sixth impedance is above the threshold impedance value, outputting instructions to apply a voltage capable of applying TTFields via the first, second, third, and fourth transducers.

Embodiment 82: A computer-implemented method for detecting an improper configuration of transducers, the transducers comprising at least a first transducer and a second transducer, the transducers being capable of applying tumor treating fields to the subject's body, the computer comprising one or more processors and memory accessible by the one or more processors, the memory storing instructions that when executed by the one or more processors cause the computer to perform the method, the method comprising: receiving a measurement of a second voltage at the second transducer resulting from a first voltage applied to the first transducer; comparing the second voltage to the first voltage; and upon determining the second voltage is over 75% of the first voltage, outputting an alert via an output device. Embodiment 83: The computer-implemented method of Embodiment 82, wherein upon determining the second voltage is over 90% of the first voltage, outputting an alert via the output device. Embodiment 84: The computer-implemented method of Embodiment 82, wherein the first voltage is between approximately 100 and 200 Volts. Embodiment 85: The computer-implemented method of Embodiment 82, wherein the first voltage is an amplitude of a first voltage signal having a frequency between 20 and 300 kHz. Embodiment 86: The computer-implemented method of Embodiment 82, further comprising: receiving a measurement of a third voltage at a third transducer resulting from the first voltage applied to the first transducer; receiving a measurement of a fourth voltage at a fourth transducer resulting from the first voltage applied to the first transducer; comparing each of the third voltage and the fourth voltage to the first voltage; and upon determining that either of the third voltage or the fourth voltage is over 75% of the first voltage, outputting an alert via the output device. Embodiment 87: The computer-implemented method of Embodiment 86, further comprising: receiving a measurement of a sixth voltage at the third transducer resulting from a fifth voltage applied to the second transducer; receiving a measurement of a seventh voltage at the fourth transducer resulting from the fifth voltage applied to the second transducer; comparing each of the sixth voltage and the seventh voltage to the fifth voltage; and upon determining that either of the sixth voltage or the seventh voltage is over 75% of the fifth voltage, outputting an alert via the output device. Embodiment 88: The computer-implemented method of Embodiment 87, further comprising: receiving a measurement of a ninth voltage at the fourth transducer resulting from an eighth voltage applied to the third transducer; comparing the ninth voltage to the eighth voltage; and upon determining that the ninth voltage is over 75% of the eighth voltage, outputting an alert via the output device.

Embodiment 89: A computer-implemented method for detecting an improper configuration of one or more of a first transducer, a second transducer, a third transducer, and a fourth transducer, the first, second, third, and fourth transducers being capable of applying tumor treating fields to a subject's body, the computer comprising one or more processors and memory accessible by the one or more processors, the memory storing instructions that when executed by the one or more processors cause the computer to perform the method, the method comprising: receiving measurements of one or more parameters of each of a second signal received at the second transducer, a third signal received at the third transducer, and a fourth signal received at the fourth transducer, each of the second, third, and fourth signals resulting from a first signal applied to the first transducer; receiving measurements of one or more parameters of each of a sixth signal received at the third transducer and a seventh signal received at the fourth transducer, each of the sixth and seventh signals resulting from a fifth signal applied to the second transducer; receiving measurements of one or more parameters of a ninth signal received at the fourth transducer resulting from an eighth signal applied to the third transducer; determining, based at least in part on the measurements of the one or more parameters, whether a short is present between any two transducers of the first, second, third, and fourth transducers; upon determining that a short is present, outputting an alert to an output device. Embodiment 90: The computer-implemented method of Embodiment 89, further comprising: upon determining that no short is present, outputting instructions to apply a voltage capable of applying tumor treating fields via the first, second, third, and fourth transducers. Embodiment 91: The computer-implemented method of Embodiment 89, wherein: the one or more parameters comprise a voltage and a current; and determining whether a short is present comprises: calculating an impedance between any two transducers of the first, second, third, and fourth transducers via the measured voltage and current values; and comparing the impedance to a threshold impedance value. Embodiment 92: The computer-implemented method of Embodiment 89, wherein: the one or more parameters comprise a voltage; and determining whether a short is present comprises: comparing a voltage applied to one of the first, second, third, and fourth transducers to a resulting voltage measured at another one of the first, second, third, and fourth transducers.

Embodiment 93: A method for detecting an improper configuration of transducers on a subject's body, the transducers comprising at least a first transducer and a second transducer, and the transducers being capable of applying tumor treating fields to the subject's body, the method comprising: sending a first voltage signal to the first transducer located on the subject's body; receiving a first resulting voltage signal at the second transducer located on the subject's body; measuring a first current and a first voltage of the first resulting voltage signal; calculating a first impedance between the first transducer and the second transducer based on the first current and the first voltage; comparing the first impedance to a threshold impedance value; and upon determining the first impedance is below the threshold impedance value, outputting an alert via an output device. Embodiment 94: The method of Embodiment 93, wherein the first and second transducers each comprise a substrate, an electrode element, and a layer of anisotropic material.

Embodiment 95: A method for detecting an improper configuration of transducers on a subject's body, the transducers comprising at least a first transducer and a second transducer, and the transducers being capable of applying tumor treating fields to the subject's body, the method comprising: applying a first voltage to the first transducer located on the subject's body; measuring a second voltage at the second transducer located on the subject's body resulting from the first voltage applied to the first transducer; comparing the second voltage to the first voltage; and upon determining the second voltage is over 75% of the first voltage, outputting an alert via an output device.

Embodiment 96: A system for delivering tumor treating fields to a subject's body, the system comprising: a transducer comprising: a substrate having a front face and a back face; at least one electrode element coupled to the substrate on a side of the front face of the substrate; an electrically conductive adhesive layer electrically coupled to the at least one electrode element, wherein the electrically conductive adhesive layer occupies an areal footprint in a plane parallel to the front face of the substrate; and a conductive wire, the wire forming a sensor in the transducer; wherein, when viewed in a direction perpendicular to the front face of the substrate: the substrate extends laterally outward beyond the areal footprint of the electrically conductive adhesive layer; and the wire substantially traces an area surrounding over 90% of the areal footprint of the electrically conductive adhesive layer.

Embodiment 97: The system of Embodiment 96, wherein, when viewed in the direction perpendicular to the front face of the substrate: the wire substantially traces an area surrounding 100% of the areal footprint of the electrically conductive adhesive layer. Embodiment 98: The system of Embodiment 96, wherein the electrically conductive adhesive layer comprises an adhesive matrix material; and a plurality of electrically conductive particles embedded at least partially within the adhesive matrix material. Embodiment 99: The system of Embodiment 98, wherein the plurality of electrically conductive particles are fibers. Embodiment 100: The system of Embodiment 98, wherein the plurality of electrically conductive particles comprise graphite. Embodiment 101: The system of Embodiment 98, wherein the plurality of electrically conductive particles comprises a sheet of fibers embedded in the adhesive matrix material. Embodiment 102: The system of Embodiment 96, further comprising a layer of anisotropic material located between one or more than one electrode element and the electrically conductive adhesive layer. Embodiment 103: The system of Embodiment 92, further comprising a second electrically conductive adhesive layer located between the one or more than one electrode element and the layer of anisotropic material. Embodiment 104: The system of Embodiment 93, wherein at least one electrically conductive adhesive layer comprises carbon fibers.

Embodiment 105: A system for delivering tumor treating fields to a subject's body, the system comprising: a transducer comprising: a substrate having a front face and a back face; at least one electrode element coupled to the substrate on a side of the front face of the substrate; a conductive material layer electrically coupled to the at least one electrode element, wherein the conductive material layer occupies an areal footprint in a plane parallel to the front face of the substrate; and a conductive wire, the wire forming a sensor in the transducer; wherein, when viewed in a direction perpendicular to the front face of the substrate: the substrate extends laterally outward beyond the areal footprint of the conductive material layer; and the wire substantially traces an area surrounding over 90% of the areal footprint of the conductive material layer.

Embodiment 106: The system of Embodiment 105, wherein the conductive material layer comprises a layer of anisotropic material or an electrically conductive adhesive layer.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A transducer apparatus for delivering tumor treating fields to a subject's body, the transducer apparatus comprising:
a substrate;
at least one electrode element coupled to the substrate;
a layer of anisotropic material electrically coupled to the at least one electrode element, wherein the at least one electrode element is located between the substrate and the layer of anisotropic material, the layer of anisotropic material having a front face and a back face, wherein the back face of the layer of anisotropic material faces the at least one electrode element;
a non-conductive material border disposed over an outer perimeter of the layer of anisotropic material, the non-conductive material border being electrically non-conductive, wherein, when viewed in a direction perpendicular to the front face of the layer of anisotropic material:
an inner edge of the non-conductive material border overlaps a portion of the front face of the layer of anisotropic material, and an outer edge of the non-conductive material border extends outside the outer perimeter of the layer of anisotropic material.

2. The transducer apparatus of claim 1, wherein, when viewed in the direction perpendicular to the front face of the layer of anisotropic material:
the inner edge of the non-conductive material border overlaps the front face of the layer of anisotropic material along an entire length of the inner edge, and
the outer edge of the non-conductive material border extends outside the outer perimeter of the layer of anisotropic material along an entire length of the non-conductive material border such that all of the outer perimeter of the layer of anisotropic material is covered by the non-conductive material border.

3. The transducer apparatus of claim 1, wherein, when viewed in a direction parallel to the front face of the layer of anisotropic material:
the non-conductive material border covers a full thickness of the layer of anisotropic material in the direction perpendicular to the front face of the layer of anisotropic material.

4. The transducer apparatus of claim 1, wherein the non-conductive material border is adhered to a front face of the substrate, the front face of the substrate facing the at least one electrode element.

5. The transducer apparatus of claim 1, wherein, when viewed in the direction perpendicular to the front face of the layer of anisotropic material:
the outer edge of the non-conductive material border extends at least 1 mm outside of the outer perimeter of the layer of anisotropic material.

6. The transducer apparatus of claim 1, wherein the non-conductive material border comprises a non-conductive adhesive.

7. The transducer apparatus of claim 1, wherein the non-conductive material border comprises a tape, bandage or plaster.

8. The transducer apparatus of claim 1, wherein the non-conductive material border comprises a tape, bandage or plaster, wherein the tape, bandage or plaster adheres to the front face, or on a front facing side, of the layer of anisotropic material within the outer perimeter of the layer of anisotropic material and is folded to adhere to the back face, or on a back facing side, of the layer of anisotropic material.

9. The transducer apparatus of claim 1, wherein the layer of anisotropic material has different thermal and/or electrical conductivities in a direction perpendicular to the front face than in directions that are parallel to the front face.

10. The transducer apparatus of claim 1, further comprising at least one of:
an electrically conductive adhesive layer located on the front face of the layer of anisotropic material between the layer of anisotropic material and the non-conductive material border, or
an electrically conductive adhesive layer located between the at least one electrode element and the back face of the layer of anisotropic material.

11. A transducer apparatus for delivering tumor treating fields to a subject's body, the transducer apparatus comprising:
a substrate having a front face and a back face;
at least one electrode element coupled to the substrate and located on a side of the front face of the substrate;
a layer of anisotropic material electrically coupled to the at least one electrode element, wherein the at least one electrode element is located between the substrate and the layer of anisotropic material; and a visual indicator that is visible from a side of the back face of the substrate;

wherein, when viewed from a direction perpendicular to the back face of the substrate:

the visual indicator indicates a border surrounding an areal exclusion zone of the transducer apparatus, the areal exclusion zone containing at least an areal footprint of the layer of anisotropic material.

12. The transducer apparatus of claim 11, wherein the visual indicator comprises at least one solid, dashed, ticked, or otherwise patterned line on the back face of the substrate, or visible from the back side of the substrate, tracing the border surrounding the areal exclusion zone.

13. The transducer apparatus of claim 12, wherein the visual indicator further comprises text on the substrate.

14. The transducer apparatus of claim 13, wherein the text identifies a region in which to cut the substrate, a region where not to cut the substrate, or both.

15. The transducer apparatus of claim 11, wherein the visual indicator comprises an area of the substrate located inside the border surrounding the areal exclusion zone having a different color or pattern than an area of the substrate located outside the border surrounding the areal exclusion zone.

16. The transducer apparatus of claim 11, wherein the visual indicator comprises a visually identifiable raised portion of the surface of the substrate along the border surrounding the areal exclusion zone due to the presence of an additional material layer coupled to the substrate.

17. A transducer apparatus for delivering tumor treating fields to a subject's body, the transducer apparatus comprising:

a substrate having a front face and a back face;

at least one electrode element coupled to the substrate and located on a side of the front face of the substrate;

a layer of anisotropic material electrically coupled to the at least one electrode element, wherein the at least one electrode element is located between the substrate and the layer of anisotropic material; and a cut-resistant material layer coupled to the substrate;

wherein, when viewed from a direction perpendicular to the front face of the substrate:

the cut-resistant material layer defines a border surrounding an areal exclusion zone of the transducer apparatus, the areal exclusion zone containing at least an areal footprint of the layer of anisotropic material.

18. The transducer apparatus of claim 17, wherein the cut-resistant material layer is configured to prevent, deter, or reduce the amount by which a user can cut through the combined substrate and cut-resistant material layer with scissors.

19. The transducer apparatus of claim 17, wherein the cut-resistant material layer is made from a thermosetting or thermoplastic polymeric material, a reinforced polymeric material, a reinforced fabric, or a combination thereof.

20. The transducer apparatus of claim 17, wherein a combined thickness of the substrate and the cut-resistant material layer is greater than 500 μm in the direction perpendicular to the front face of the substrate.

* * * * *